US011426582B1

(12) United States Patent
Smyth et al.

(10) Patent No.: US 11,426,582 B1
(45) Date of Patent: Aug. 30, 2022

(54) PROGRESSIVE INSERTION MIDDLE EAR PROTECTOR

(71) Applicant: Cochlear Limited, Macquarie University (AU)

(72) Inventors: Daniel Smyth, Dublin (IE); Nicholas Pawsey, North Ryde (AU); Peter Gibson, South Coogee (AU)

(73) Assignee: Cochlear Limited, Macquarie University (AU)

( * ) Notice: Subject to any disclaimer, the term of this patent is extended or adjusted under 35 U.S.C. 154(b) by 176 days.

(21) Appl. No.: 16/417,234

(22) Filed: May 20, 2019

Related U.S. Application Data

(60) Provisional application No. 62/674,775, filed on May 22, 2018.

(51) Int. Cl.
*A61N 1/00* (2006.01)
*A61N 1/36* (2006.01)
*A61N 1/05* (2006.01)

(52) U.S. Cl.
CPC ....... *A61N 1/36038* (2017.08); *A61N 1/0541* (2013.01)

(58) Field of Classification Search
CPC . A61N 1/36038; A61N 1/0541; H04R 25/606
See application file for complete search history.

(56) References Cited

U.S. PATENT DOCUMENTS

| | | | |
|---|---|---|---|
| 7,966,077 B2 * | 6/2011 | Risi | A61N 1/0541 607/57 |
| 8,452,411 B2 | 5/2013 | Risi | |
| 8,751,019 B2 | 6/2014 | Dadd et al. | |
| 9,375,565 B2 | 6/2016 | Pawsey et al. | |
| 9,597,503 B2 | 3/2017 | Risi et al. | |
| 9,713,713 B2 | 7/2017 | Vancaillie et al. | |
| 2015/0374964 A1 * | 12/2015 | Verhoeven | A61M 5/148 604/140 |
| 2017/0120044 A1 * | 5/2017 | Pawsey | A61N 1/0541 |
| 2019/0054303 A1 * | 2/2019 | Rashidi | A61B 17/3468 |
| 2020/0171301 A1 * | 6/2020 | Koka | A61N 1/08 |

* cited by examiner

*Primary Examiner* — Gary Jackson
*Assistant Examiner* — Anant A Gupta
(74) *Attorney, Agent, or Firm* — Knobbe, Martens, Olson & Bear, LLP

(57) ABSTRACT

An apparatus includes a stimulation assembly having an elongate body and a plurality of stimulation elements longitudinally spaced from one another along a portion of the elongate body. The stimulation assembly includes a first set of the stimulation elements and a second set of the stimulation elements. The apparatus further includes a tube over the second set of the stimulation elements. The tube is configured to be removed from the stimulation assembly.

31 Claims, 19 Drawing Sheets

PROGRESSIVE INSERTION MIDDLE EAR PROTECTOR

BACKGROUND

Field

The present application relates generally to cochlear-implanted auditory prostheses, and more specifically systems and methods for facilitating progressive insertion of stimulation elements of such auditory prostheses.

Description of the Related Art

Hearing loss, which may be due to many different causes, is generally of two types, conductive and/or sensorineural. Conductive hearing loss occurs when the normal mechanical pathways of the outer and/or middle ear are impeded, for example, by damage to the ossicular chain or ear canal. Sensorineural hearing loss occurs when there is damage to the inner ear, or to the nerve pathways from the inner ear to the brain.

Individuals who suffer from conductive hearing loss typically have some form of residual hearing because the hair cells in the cochlea are undamaged. As a result, individuals suffering from conductive hearing loss might receive an auditory prosthesis that generates mechanical motion of the cochlea fluid instead of a hearing aid based on the type of conductive loss, amount of hearing loss and customer preference. Such prostheses include, for example, bone conduction devices and direct acoustic stimulators.

In many people who are profoundly deaf, however, the reason for their deafness is sensorineural hearing loss. Those suffering from some forms of sensorineural hearing loss are unable to derive suitable benefit from auditory prostheses that generate mechanical motion of the cochlea fluid. Such individuals can benefit from implantable auditory prostheses that stimulate nerve cells of the recipient's auditory system in other ways (e.g., electrical, optical, and the like). Cochlear implants are often proposed when the sensorineural hearing loss is due to the absence or destruction of the cochlea hair cells, which transduce acoustic signals into nerve impulses. Auditory brainstem stimulators might also be proposed when a recipient experiences sensorineural hearing loss due to damage to the auditory nerve.

SUMMARY

In one aspect disclosed herein, an apparatus is provided. The apparatus comprises a stimulation assembly comprising an elongate body and a plurality of stimulation elements longitudinally spaced from one another along a portion of the elongate body. The stimulation assembly comprises a first set of the stimulation elements and a second set of the stimulation elements. The apparatus further comprises a tube over the second set of the stimulation elements. The tube is configured to be removed from the stimulation assembly.

In another aspect disclosed herein, an apparatus is provided. The apparatus comprises a stimulation assembly comprising a plurality of stimulation elements configured to provide stimulation signals to a cochlea of a recipient. The plurality of stimulation elements comprises a first set of stimulation elements configured to be positioned within the cochlea during a first surgical procedure and a second set of stimulation elements configured to be positioned within a middle ear region of the recipient externally to the cochlea during the first surgical procedure. The apparatus further comprises a tube over the second set of stimulation elements. The tube is configured to remain within the middle ear region after the first surgical procedure and to be removed from the stimulation assembly during a second surgical procedure.

In still another aspect disclosed herein, a method is provided. The method comprises providing an elongate stimulation assembly comprising a plurality of stimulation elements and a tube. The plurality of stimulation elements is configured to stimulate spiral ganglion cells of a cochlea of a recipient and comprise a first set of stimulation elements and a second set of stimulation elements. The tube covers the second set of stimulation elements and does not cover the first set of stimulation elements, the tube configured to be removed from the stimulation assembly. The method further comprises implanting the stimulation assembly such that the first set of stimulation elements are positioned within the cochlea and the second set of stimulation elements and the tube are positioned within a middle ear region of the recipient externally to the cochlea.

In still another aspect disclosed herein, a method is provided. The method comprises providing an elongate stimulation assembly comprising a plurality of stimulation elements and a tube. The plurality of stimulation elements is configured to stimulate spiral ganglion cells of a cochlea of a recipient. The tube covers some of the stimulation elements but fewer than all of the stimulation elements, and is configured to be removed from the stimulation assembly. The method further comprises implanting the stimulation assembly within the cochlea of a recipient such that the tube is positioned externally to the cochlea. The stimulation assembly is positioned within the cochlea so as to allow residual hearing in a first frequency range using the cochlea while the stimulation assembly is configured to assist hearing in a second frequency range using the cochlea, the second frequency range higher than the first frequency range.

In still another aspect disclosed herein, a method is provided. The method comprises providing an implanted stimulation assembly comprising a first set of stimulation elements within a cochlea of a recipient, a second set of stimulation elements external to the cochlea, and a tube covering the second set of stimulation elements. The tube is configured to be removed from the stimulation assembly. The method further comprises removing the tube from the stimulation assembly. The method further comprises moving the stimulation assembly further into the cochlea such that both the first set of stimulation elements and the second set of stimulation elements are positioned within the cochlea.

BRIEF DESCRIPTION OF THE DRAWINGS

Embodiments are described herein in conjunction with the accompanying drawings, in which.

DETAILED DESCRIPTION

Certain embodiments described herein provide a system and method for progressive insertion of a stimulation assembly in the cochlea of a recipient up to a nominal, incomplete depth of insertion (e.g., for the purpose of preserving residual hearing by the recipient and/or not disturbing the cochlear structure in the apical regions of the cochlea), and subsequently moving the stimulation assembly further into the cochlea to a greater depth (e.g., if residual hearing is lost or if performance of the auditory prosthesis is unsatisfactory). While the initial implantation of the stimulation assembly and the other implanted components of the auditory prosthesis is generally performed during a surgical procedure which can be highly invasive (e.g., with the recipient under a general anesthetic), subsequently moving the stimulation assembly further into the cochlea can potentially be performed during a subsequent surgical procedure which can be less invasive (e.g., with the recipient under a local anesthetic).

Certain embodiments described herein advantageously provide a stimulation assembly comprising a tube that is configured to cover the stimulation elements (e.g., electrodes; contacts) that remain in the middle ear region after the initial implantation of the auditory prosthesis and may be subsequently advanced into the cochlea. The tube is further configured to be removed from the stimulation assembly during the subsequent surgical procedure prior to moving the stimulation assembly further into the cochlea. In certain such embodiments, the tube can mitigate potential risks associated with the progressive insertion of the stimulation assembly, such as protecting against damage to the stimulation elements that remain in the middle ear region due to the formation of fibrosis tissue, and protecting against the introduction of bacteria (e.g., a biofilm) into the cochlea. This introduction of bacteria into the cochlea may otherwise lead to chronic infection of the cochlea (which can be poorly treatable by antibiotics) and associated downstream risks of meningitis from an intractable infection of the inner ear in communication with the cerebrospinal fluid.

Figure 1A:
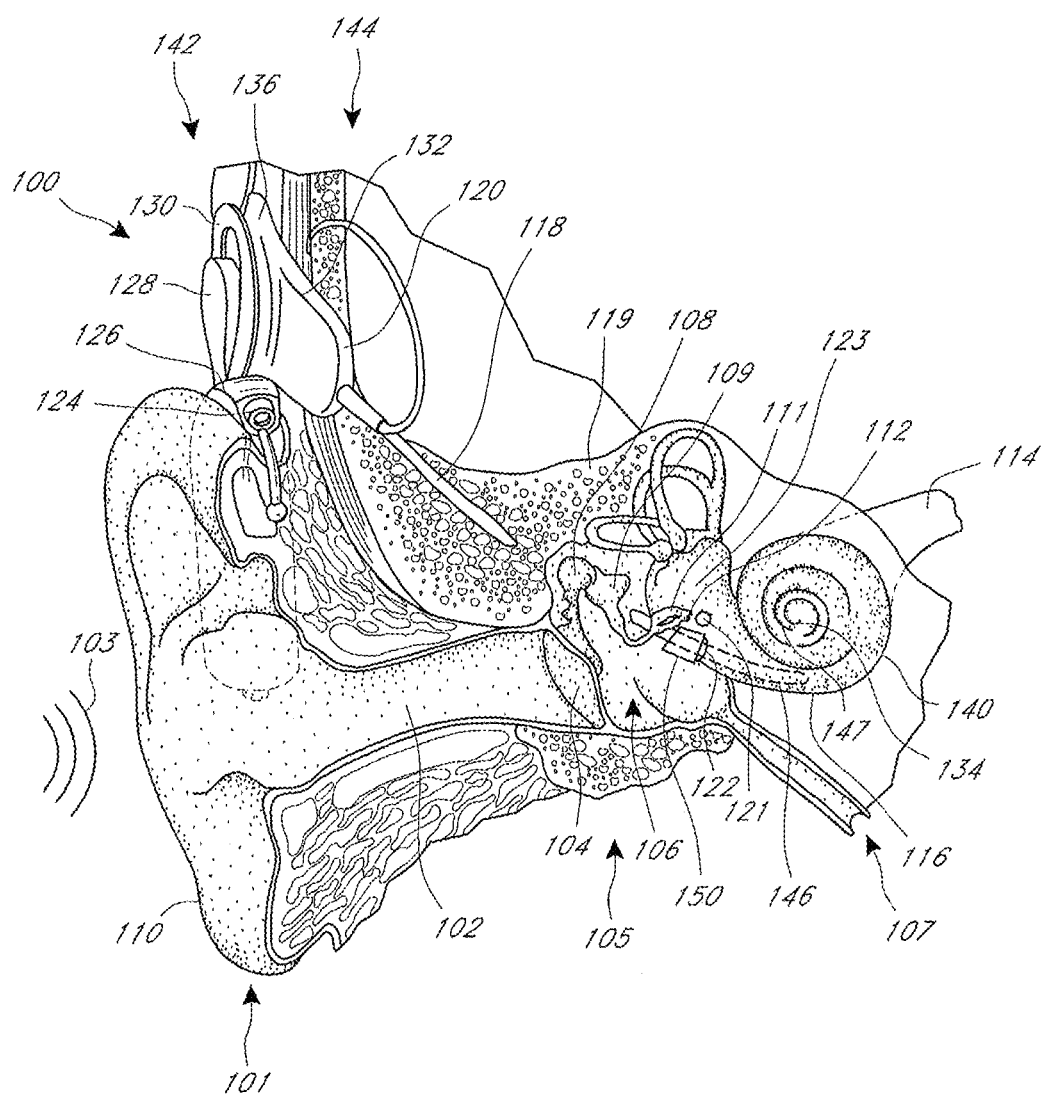
FIG. 1A is a perspective view of an example auditory prosthesis implanted in a recipient with a stimulation assembly partially inserted into the cochlea and comprising a tube in accordance with certain embodiments described herein.
Figure 1B:
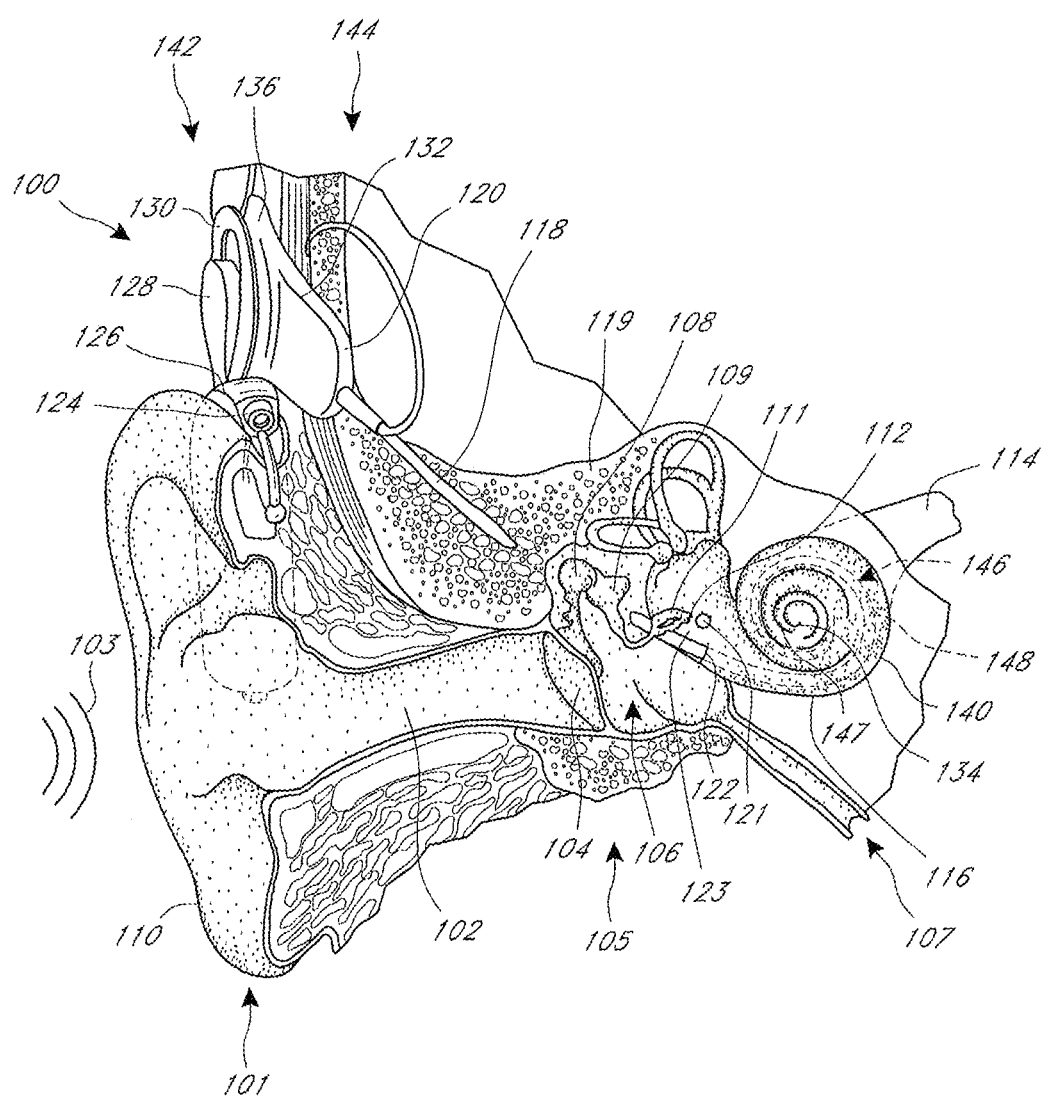
FIG. 1B is a perspective view of the example auditory prosthesis of FIG. 1A with the stimulation assembly moved further into the cochlea after the tube has been removed from the stimulation assembly in accordance with certain embodiments described herein.

FIG. 1A is a perspective view of an example auditory prosthesis 100 (e.g., cochlear implant), implanted in a recipient with a stimulation assembly 118 partially inserted into the cochlea 140 and comprising a tube 150 in accordance with certain embodiments described herein. FIG. 1B is a perspective view of the example auditory prosthesis 100 of FIG. 1A with the stimulation assembly 118 moved further into the cochlea 140 after the tube 150 has been removed from the stimulation assembly 118 in accordance with certain embodiments described herein.

As shown in FIGS. 1A and 1B, the recipient has an outer ear 101, a middle ear 105, and an inner ear 107. In a fully functional ear, the outer ear 101 comprises an auricle 110 and an ear canal 102. An acoustic pressure or sound wave 103 is collected by the auricle 110 and is channeled into and through the ear canal 102. Disposed across the distal end of the ear canal 102 is a tympanic membrane 104 which vibrates in response to the sound wave 103. This vibration is coupled to oval window or fenestra ovalis 112 through three bones of middle ear 105, collectively referred to as the ossicles 106 and comprising the malleus 108, the incus 109, and the stapes 111. The bones 108, 109, and 111 of the middle ear 105 serve to filter and amplify the sound wave 103, causing the oval window 112 to articulate, or vibrate in response to vibration of the tympanic membrane 104. This vibration sets up waves of fluid motion of the perilymph within the cochlea 140. Such fluid motion, in turn, activates tiny hair cells (not shown) inside the cochlea 140. Activation of the hair cells causes appropriate nerve impulses to be generated and transferred through the spiral ganglion cells (not shown) and auditory nerve 114 to the brain (also not shown) where they are perceived as sound.

As shown in FIGS. 1A and 1B, the example auditory prosthesis 100 comprises one or more components which are temporarily or permanently implanted in the recipient. The example auditory prosthesis 100 is shown in FIGS. 1A and 1B with an external component 142 which is directly or indirectly attached to the recipient's body, and an internal component 144 which is temporarily or permanently implanted in the recipient (e.g., positioned in a recess of the temporal bone adjacent to the auricle 110 of the recipient). The external component 142 typically comprises one or more sound input elements (e.g., an external microphone 124) for detecting sound, a sound processing unit 126 (e.g., disposed in a Behind-The-Ear unit), a power source (not shown), and an external transmitter unit 128. In the illustrative embodiments of FIGS. 1A and 1B, the external transmitter unit 128 comprises an external coil 130 (e.g., a wire antenna coil comprising multiple turns of electrically insulated single-strand or multi-strand platinum or gold wire) and, preferably, a magnet (not shown) secured directly or indirectly to the external coil 130. The external coil 130 of the external transmitter unit 128 is part of an inductive radio frequency (RF) communication link with the internal component 144. The sound processing unit 126 processes the output of the microphone 124 that is positioned externally to the recipient's body, in the depicted embodiment, by the recipient's auricle 110. The sound processing unit 126 generates encoded signals, sometimes referred to herein as encoded data signals, which are provided to the external transmitter unit 128 (e.g., via a cable).

The power source of the external component 142 is configured to provide power to the auditory prosthesis 100, where the auditory prosthesis 100 includes a battery (e.g., located in the internal component 144, or disposed in a separate implanted location) that is recharged by the power provided from the external component 142 (e.g., via a transcutaneous energy transfer link). The transcutaneous energy transfer link is used to transfer power and/or data to the internal component 144 of the auditory prosthesis 100. Various types of energy transfer, such as infrared (IR), electromagnetic, capacitive, and inductive transfer, may be used to transfer the power and/or data from the external component 142 to the internal component 144. During operation of the auditory prosthesis 100, the power stored by the rechargeable battery is distributed to the various other implanted components as needed.

The internal component 144 comprises an internal receiver unit 132, a stimulator unit 120, and an elongate stimulation assembly 118. In some embodiments, the internal receiver unit 132 and the stimulator unit 120 are hermetically sealed within a biocompatible housing, sometimes collectively referred to as a stimulator/receiver unit. The internal receiver unit 132 comprises an internal coil 136 (e.g., a wire antenna coil comprising multiple turns of electrically insulated single-strand or multi-strand platinum or gold wire), and preferably, a magnet (also not shown) fixed relative to the internal coil 136. The internal coil 136 receives power and/or data signals from the external coil 130 via a transcutaneous energy transfer link (e.g., an inductive RF link). The stimulator unit 120 generates electrical stimulation signals based on the data signals, and the stimulation signals are delivered to the recipient via the elongate stimulation assembly 118.

The elongate stimulation assembly 118 has a proximal end connected to the stimulator unit 120, and a distal end implanted in the cochlea 140. The stimulation assembly 118 extends from the stimulator unit 120 to the cochlea 140 through the mastoid bone 119. In some embodiments, the stimulation assembly 118 may be implanted at least in the basal region 116, and sometimes further. For example, the stimulation assembly 118 may extend towards the apical end of the cochlea 140, referred to as the cochlea apex 134. In certain circumstances, the stimulation assembly 118 may be inserted into the cochlea 140 via a cochleostomy 122. In other circumstances, a cochleostomy 122 may be formed through the round window 121, the oval window 112, the promontory 123, or through an apical turn 147 of the cochlea 140.

The elongate stimulation assembly 118 comprises a longitudinally aligned and distally extending array 146 (e.g., electrode array; contact array) of stimulation elements 148 (e.g., electrical electrodes; electrical contacts; optical emitters; optical contacts). The stimulation elements 148 are longitudinally spaced from one another along a length of the elongate body of the stimulation assembly 118. For example, the stimulating assembly 118 can comprise an array 146 comprising twenty-two (22) stimulation elements 148 that are configured to deliver stimulation to the cochlea 140. Although the array 146 of stimulation elements 148 can be disposed on the stimulation assembly 118, in most practical applications, the array 146 is integrated into the stimulation assembly 118 (e.g., the stimulation elements 148 of the array 146 are disposed in the stimulation assembly 118). As noted, the stimulator unit 120 generates stimulation signals (e.g., electrical signals; optical signals) which are applied by the stimulation elements 148 to the cochlea 140, thereby stimulating the auditory nerve 114.

A variety of types of intra-cochlear stimulation assemblies 118 are compatible with certain embodiments described herein, including but not limited to: short, straight, and perimodiolar. A perimodiolar stimulation assembly 118 is configured to adopt a curved configuration during and/or after implantation into the cochlea 140. To achieve this, in certain embodiments, the perimodiolar stimulation assembly 118 is pre-curved to the same general curvature of the cochlea 140. Such examples of the stimulation assembly 118 can be held straight by, for example, a stiffening stylet (not shown) or sheath which is removed during implantation, or alternatively varying material combinations or the use of shape memory materials, so that the stimulation assembly 118 may adopt its curved configuration when in the cochlea 140. Other methods of implantation, as well as other stimulation assemblies 118 which adopt a curved configuration, may be used. The stimulation assembly 118 of certain other embodiments comprises a non-perimodiolar stimulation assembly 118. For example, the stimulation assembly 118 can comprise a straight stimulation assembly 118 or a mid-scala assembly which assumes a mid-scala position during or following implantation. Alternatively, the stimulation assembly 118 can comprise a short electrode implanted into at least the basal region of the cochlea 140.

Figure 2:
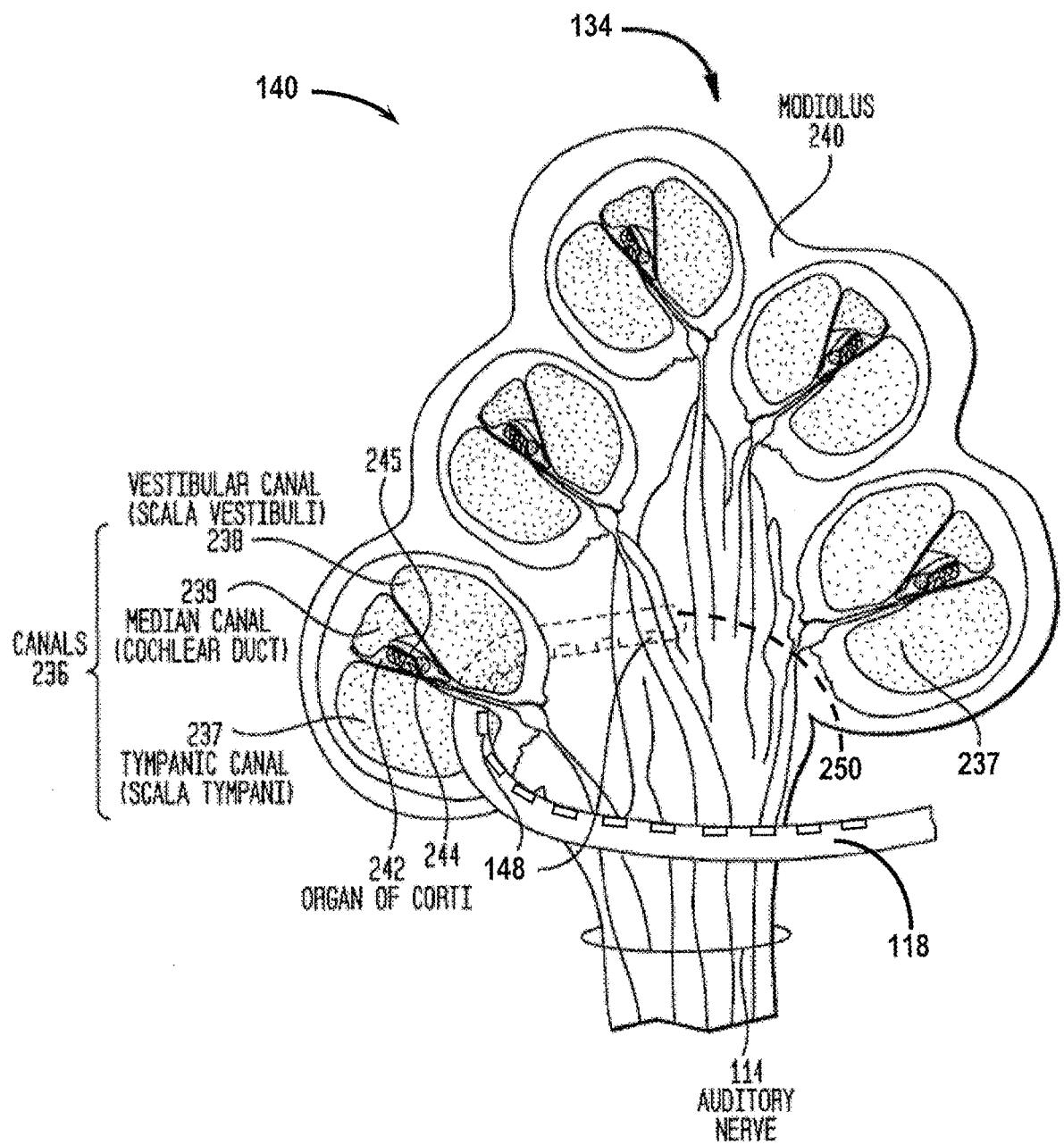
FIG. 2 is cross-sectional view of the cochlea illustrating the stimulating assembly partially implanted therein in accordance with certain embodiments described herein.

FIG. 2 is cross-sectional view of the cochlea 140 illustrating the stimulating assembly 118 partially implanted therein in accordance with certain embodiments described herein. The stimulation assembly 118 is also shown in FIG. 2, although without showing the tube 150 and only showing a subset of the stimulation elements 148. The cochlea 140 is a conical spiral structure that comprises three parallel fluid-filled canals or ducts, collectively and generally referred to herein as canals 236. Canals 236 comprise the tympanic canal 237, also referred to as the scala tympani 237, the vestibular canal 238, also referred to as the scala vestibuli 238, and the median canal 239, also referred to as the scala media 239. The cochlea 140 includes the modiolus 240 which is a conical shaped central region around which the cochlea canals 236 spiral. The modiolus 240 consists of spongy bone in which the cochlea nerve cells, sometimes referred to herein as the spiral ganglion cells, are situated. The cochlea canals 236 generally turn 2.5 times around the modiolus 240.

In normal hearing, sound entering the auricle 110 (see, e.g., FIG. 1) causes pressure changes in the cochlea 140 that travel through the fluid-filled tympanic and vestibular canals 237, 238. The organ of Corti 242, which is situated on the basilar membrane 244 in scala media 239, contains rows of hair cells (not shown) which protrude from its surface. Located above the hair cells is the tectoral membrane 245 which moves in response to pressure variations in the fluid-filled tympanic and vestibular canals 237, 238. Small relative movements of the layers of membrane 245 are sufficient to cause the hair cells to move, thereby causing the creation of a voltage pulse or action potential which travels along the associated nerve fibers that connect the hair cells with the auditory nerve 114. The auditory nerve 114 relays the impulses to the auditory areas of the brain (not shown) for processing.

Typically, in cochlear implant recipients, some portion of the cochlea 140 (e.g., the hair cells) is damaged such that the cochlea 140 cannot transduce pressure changes into nerve impulses for relay to the brain. As such, the stimulating elements 148 of the stimulating assembly 118 are used to directly stimulate the cells to create nerve impulses resulting in perception of a received sound (e.g., to evoke a hearing precept).

To insert the intra-cochlear stimulating assembly 118 into the cochlea 140, an opening (facial recess) is created through the recipient's mastoid bone 119 (see, e.g., FIG. 1) to access the recipient's middle ear cavity 106 (see, e.g., FIG. 1). An opening is then created from the middle ear 106 into the cochlea 140 through, for example, the round window 121, oval window 112, the promontory 123, etc. of the cochlea 140. The stimulating assembly 118 is then gently advanced (e.g., pushed) forward into the cochlea 140 until the stimulating assembly 118 achieves the implanted position. As shown in FIGS. 1A, 1B, and 2, the stimulating assembly 118 follows the helical shape of the cochlea 140. That is, the stimulating assembly 118 spirals around the modiolus 240.

The effectiveness of the stimulation by the stimulation assembly 118 depends, at least in part, on the place along the basilar membrane 244 where the stimulation is delivered. That is, the cochlea 140 has characteristically been referred to as being "tonotopically mapped," in that regions of the cochlea 140 toward the basal end are more responsive to high frequency signals, while regions of cochlea 140 toward the apical end are more responsive to low frequency signals. These tonotopical properties of the cochlea 140 are exploited in a cochlear implant by delivering stimulation within a predetermined frequency range to a region of the cochlea 140 that is most sensitive to that particular frequency range. However, this stimulation relies on the particular stimulation elements 148 having a final implanted positioned adjacent to a corresponding tonotopic region of the cochlea 140 (e.g., a region of the cochlea 140 that is sensitive to the frequency of sound represented by the stimulation element 148).

To achieve a selected final implanted position, the distal end/tip 250 of the stimulation assembly 118 is placed at a selected angular position (e.g., angular insertion depth). As used herein, the angular position or angular insertion depth of the stimulation assembly 118 refers to the angular rotation of the distal end 250 of the stimulation assembly 118 from the cochleostomy 122 (e.g., round window 121) through which the stimulation assembly 118 enters the cochlea 140. As such, the angular position/angular insertion depth may be expressed in terms of how many angular degrees the distal end 250 of the stimulation assembly 118 has traveled within the cochlea 140 with respect to the cochleostomy 122. For example, an angular insertion depth of one hundred and eighty (180) degrees indicates that the distal end 250 of the stimulation assembly 118 has traveled around half (½) of the first turn of the cochlea 140. An angular insertion depth of three hundred and sixty (360) degrees indicates that the distal end 250 of the stimulation assembly 118 has traveled completely around the first turn of the cochlea 140.

In certain embodiments, the stimulation assembly 118 is implanted (e.g., during a first surgical procedure) with a first set of the stimulation elements 148 within the cochlea 140 and a second set of the stimulation elements 148 outside the cochlea 140 (e.g., within the middle ear region 106). For example, such implantation of the stimulation assembly 118 in the cochlea 140 of the recipient up to a nominal, incomplete depth of insertion can be performed for the purpose of preserving residual hearing by the recipient and/or for not disturbing the cochlear structure in the apical regions of the cochlea 140. During a first surgical procedure, the stimulation assembly 118 is inserted into the cochlea 140 to a first angular insertion depth (e.g., with the most distal/apical stimulation element 148 spaced away from the cochlea apex 134, as shown in FIGS. 1A and 2). After the first surgical procedure, the first set of stimulation elements 148 are configured to stimulate some of the spiral ganglion cells of the cochlea 140 while the second set of stimulation elements 148 remain unused. In certain such embodiments, the stimulation assembly 118 is positioned within the cochlea 140 so as to allow residual hearing in a first frequency range using the cochlea 140 (e.g., using the spiral ganglion cells of the cochlea 140 in a portion of the cochlea 140 at a greater angular insertion depth than that of the distal end 250 of the stimulation assembly 118 and that are not stimulated by the first set of stimulation elements 148) while the stimulation assembly 118 is configured to assist hearing in a second frequency range (e.g., higher than the first frequency range) using the cochlea 140 (e.g., using the spiral ganglion cells of the cochlea 140 in a portion of the cochlea 140 at a lesser angular insertion depth than that of the distal end 250 of the stimulation assembly 118 and that are stimulated by the first set of stimulation elements 148). This first surgical procedure (e.g., during which the stimulation assembly 118 is initially implanted, along with the implantation of the other implanted components of the auditory prosthesis 100) can be highly invasive (e.g., with the recipient under a general anesthetic).

In certain embodiments, if residual hearing is lost or if performance of the auditory prosthesis 100 after the first surgical procedure is unsatisfactory, the stimulation assembly 118 is subsequently repositioned to extend further into the cochlea 140 by repositioning the distal end 250 of the stimulation assembly 118 to a second angular insertion depth greater than the first angular insertion depth (e.g., to a complete depth within the cochlea 140). This positioning and subsequent repositioning of the stimulation assembly 118 is referred to herein as "progressive insertion." After this repositioning, the second set of stimulation elements 148, which remained outside the cochlea 140 after the first surgical procedure, are within the cochlea 140 such that both the first set of stimulation elements 148 and the second set of stimulation elements 148 are positioned to stimulate the spiral ganglion cells of the cochlea 140 (e.g., with the stimulation assembly 118 inserted into the cochlea 140 to its full operational depth). The repositioning of the stimulation assembly 118 can be performed during a second surgical procedure which is subsequent to and can be less invasive (e.g., with the recipient under a local anesthetic) than the first surgical procedure during which the stimulation assembly 118 and the other implantable components of the auditory prosthesis 100 were initially implanted. For example, the second surgical procedure can be performed by accessing the middle ear region 106 and the stimulation assembly 118 through the ear canal 102 and through the region of the tympanic membrane 104 (e.g., via puncture and/or removal of the tympanic membrane 104).

FIGS. 3A-3E schematically illustrate example tubes 150 as a portion of an example apparatus 300 (e.g., auditory prosthesis 100; cochlear implant) in accordance with certain embodiments described herein. The apparatus 300 comprises a stimulation assembly 118 comprising an elongate body 310 and a plurality of stimulation elements 148. For example, the stimulation assembly 118 can comprise an elongate electrode array and the plurality of stimulation elements 148 can comprise a plurality of electrical electrodes, electrical contacts, optical emitters, and/or optical contacts. The stimulation elements 148 are longitudinally spaced from one another along a portion of the elongate body 310. The stimulation assembly 118 is configured to be implanted such that a first set 312 of the stimulation elements 148 is within the cochlea 140 (e.g., within the fluid of the scala tympani 237 of the cochlea 140) and a second set 314 of the stimulation elements 148 is outside the cochlea 140 (e.g., in the middle ear region 106). The first set 312 of the stimulation elements 148 is configured to provide stimulation signals to the cochlea 140 (e.g., to the spiral ganglion cells of the cochlea 140).

The apparatus 300 further comprises a tube 150 (e.g., protective tubular structure; sleeve) over the second set 314 of the stimulation elements 148. The tube 150 is configured to be removed from the stimulation assembly 118 while the first set 312 of the stimulation elements 148 is within the cochlea 140 and the second set 314 of the stimulation elements 148 is outside the cochlea 140. While certain embodiments are described herein with the stimulation assembly 118 and the tube 150 being separate components of the apparatus 100, in certain embodiments, the stimulation assembly 118 comprises the tube 150 (e.g., the tube 150 is a component of the stimulation assembly 118).

The stimulation assembly 118 is configured to be inserted (e.g., during a first surgical procedure) into the cochlea 140 via a cochleostomy 122 through a bony wall 316 of the cochlea 140 (e.g., formed through the round window 121, the oval window 112, the promontory 123, or through an apical turn 147 of the cochlea 140). Once implanted (e.g., during the first surgical procedure), the stimulation assembly 118 extends towards the cochlea apex 134 with the first set 312 of the stimulation elements 148 within the cochlea 140 (e.g., within the fluid of the scala tympani 237 of the cochlea 140) and with the second set 314 of the stimulation elements 148 and the tube 150 within the middle ear region 106 outside the cochlea 140 (e.g., positioned externally to the cochlea 140).

Figure 3A:
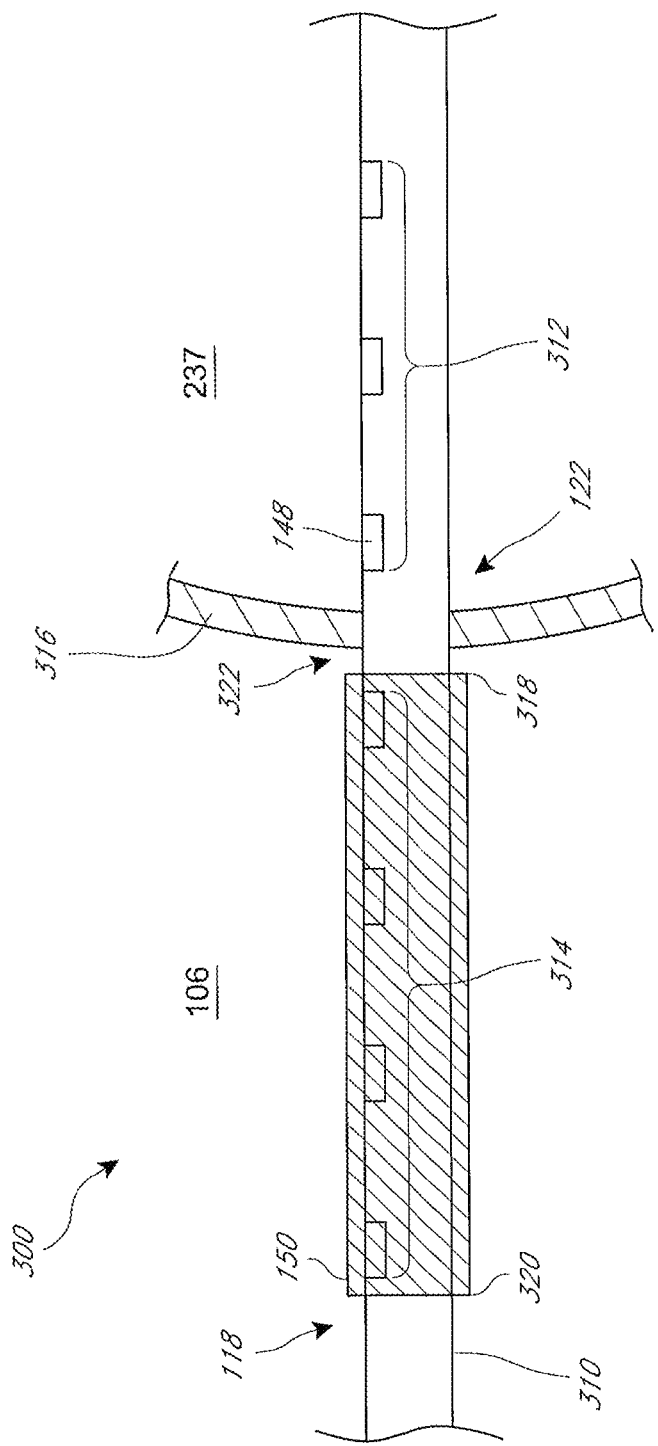
FIGS. 3A-3E schematically illustrate example tubes as a portion of an example apparatus in accordance with certain embodiments described herein.
Figure 3B:
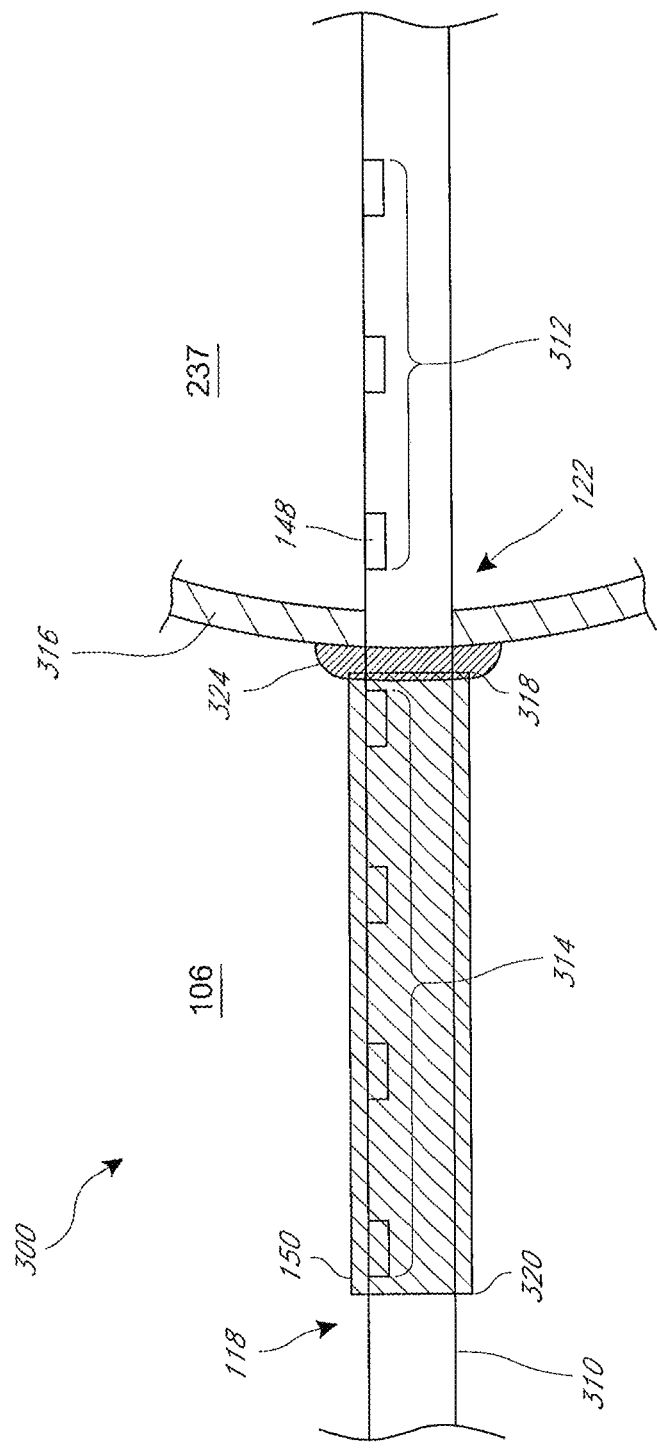

The tube 150 comprises a first end portion 318 positioned at or near (e.g., proximal to) the bony wall 316 of the cochlea 140 and a second end portion 320 positioned away from the bony wall 316 of the cochlea 140. As schematically illustrated by FIG. 3A, in certain embodiments, the tube 150 is positioned such that the first end portion 318 does not contact the bony wall 316 of the cochlea 140, with a gap 322 (e.g., at least 0.5 millimeter; at least 1 millimeter) between the first end portion 318 and the bony wall 316. In certain such embodiments, tissue 324 can be positioned around the first end portion 318 such that the tissue 324 extends across the gap 322 and contacts both the first end portion 318 and the bony wall 316 (e.g., during the first surgical procedure) to form a bacteria-resistant barrier (e.g., seal) configured to prevent bacteria from entering the cochlea 140 through the cochleostomy 122, as schematically illustrated by FIG. 3B. For example, the tissue 324 can comprise tissue placed into position during the first surgical procedure and/or can comprise fibrosis tissue that forms after the first surgical procedure during which the apparatus 100 is implanted.

Figure 3C:
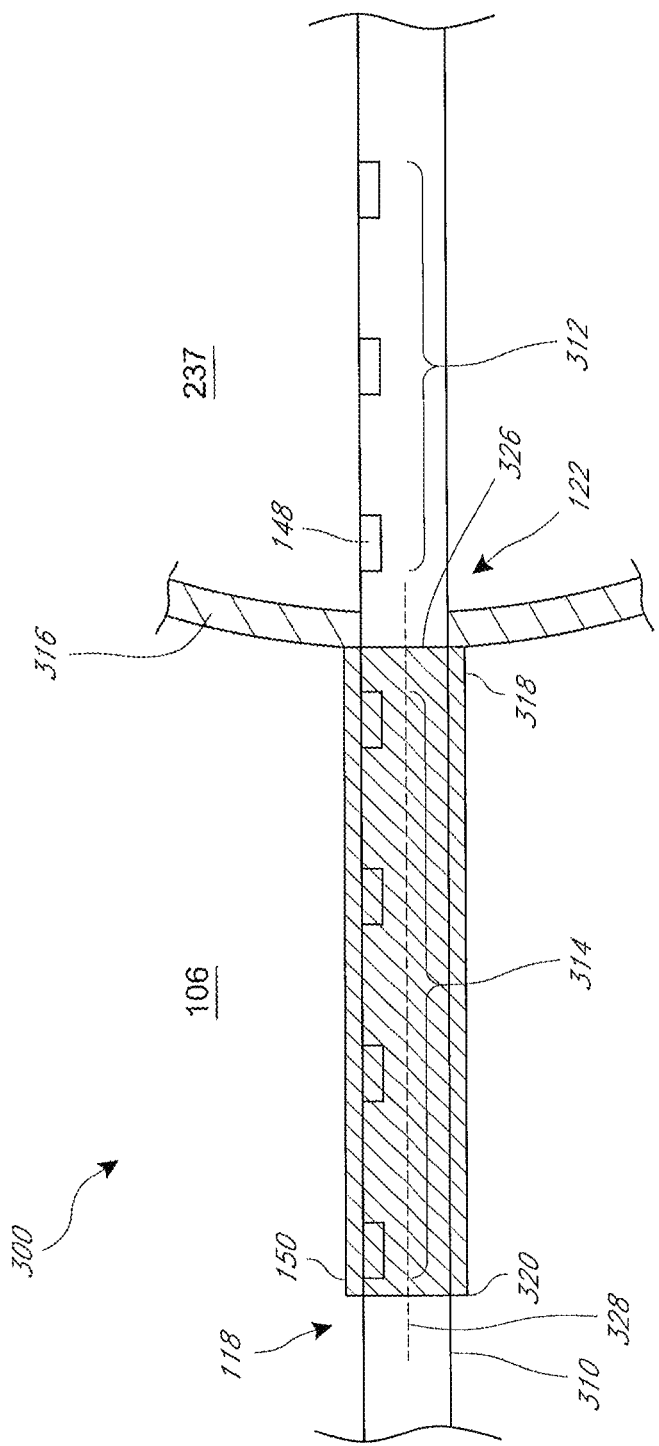

In certain embodiments, the first end portion 318 is configured to contact an outer surface of the cochlea 140 (e.g., an outer surface of the bony wall 316) to form a bacteria-resistant barrier (e.g., seal) configured to inhibit (e.g., prevent) bacteria from entering the cochlea 140. In certain such embodiments, there is no gap between a first end portion 318 and the bony wall 316 through which bacteria can enter the cochlea 140 via the cochleostomy 122. For example, as schematically illustrated by FIG. 3C, the first end portion 318 can have an end surface 326 that contacts the bony wall 316. In certain such embodiments, the end surface 326 of certain embodiments is oriented at an angle (e.g., 30 degrees; 45 degrees; 90 degrees; 120 degrees; 135 degrees) relative to a longitudinal axis 328 of the tube 150, and the angle can be configured to match an angle of the outer surface of the bony wall 316 in the region surrounding the cochleostomy 122 (e.g., round window 121).

For example, as schematically illustrated by FIG. 3C, the end surface 326 is oriented at an angle of 120 degrees relative to the longitudinal axis 328, and matches an angle of the outer surface of the bony wall 316.

Figure 3D:
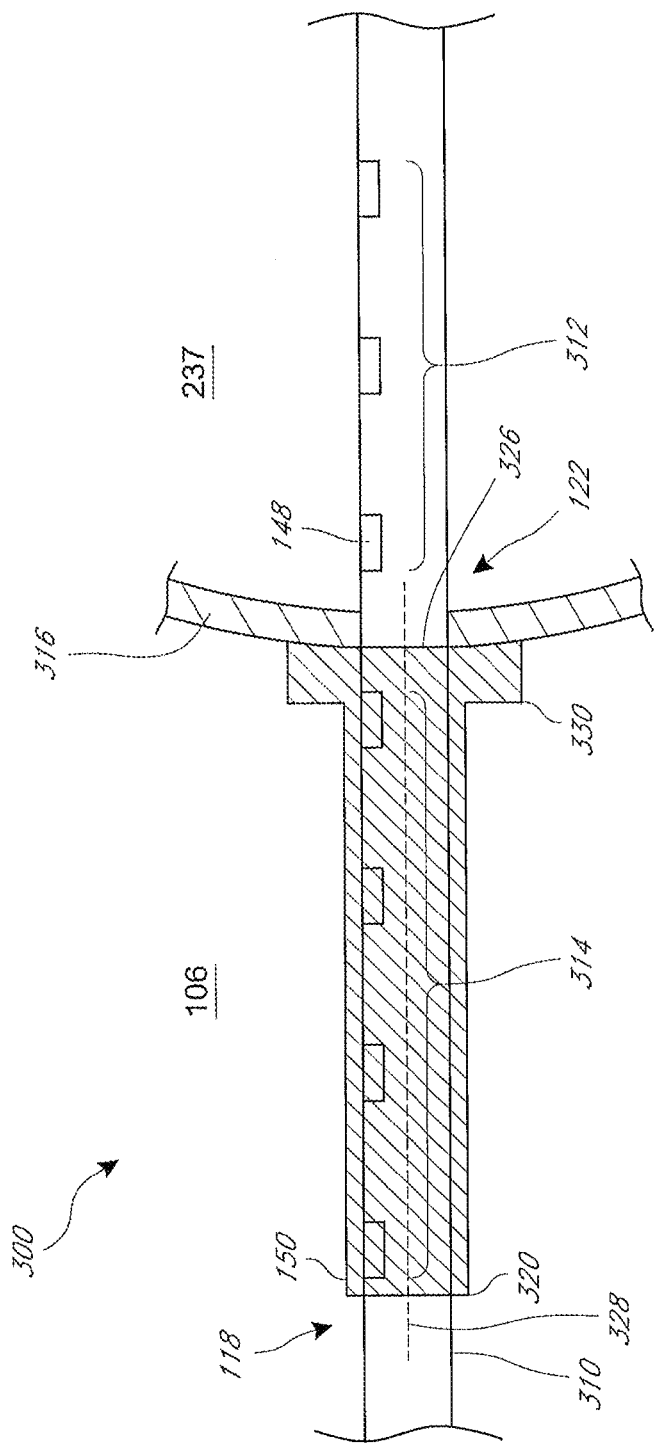
Figure 3E:
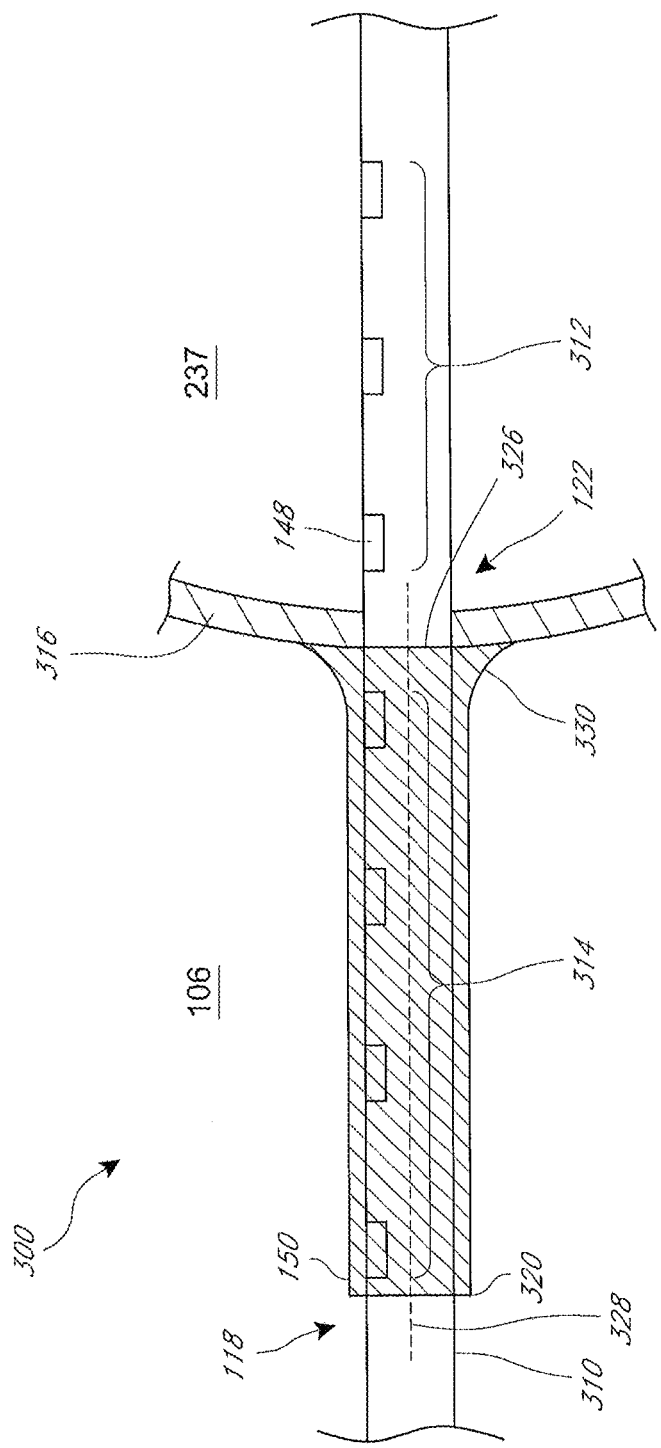

In certain embodiments, the first end portion 318 extends outwards in a direction away from (e.g., generally perpendicular to) the longitudinal axis 328 of the tube 150, as schematically illustrated by FIGS. 3D and 3E. In certain such embodiments, the first end portion 318 comprises one or more protrusions 330 (e.g., a flange) extending outwards in a direction away from (e.g., generally perpendicular to) the longitudinal axis 328, as schematically illustrated by FIG. 3D. In certain other such embodiments, the first end portion 318 is configured to expand in a radial direction (e.g., generally perpendicular to the longitudinal axis 328) along the outer surface of the cochlea 140 while positioned proximally to the bony wall 316 of the cochlea 140, as schematically illustrated by FIG. 3E. For example, the first end portion 318 can be configured to splay outwardly in response to being pressed against the bony wall 316 with sufficient force (e.g., during the first surgical procedure) to plastically deform the first end portion 318. For another example, the first end portion 318 can be configured to expand outwardly in response to moisture, temperature, or other physical effect to which the first end portion 318 is exposed. In certain embodiments, the first end portion 318 (e.g., as shown in FIGS. 3B-3E) is part of the bacteria-resistant barrier (e.g., seal) and is configured to allow fibrosis tissue to form as part of the bacteria-resistant barrier (e.g., seal) after the first surgical procedure during which the apparatus 100 is implanted.

In certain embodiments, the tube 150 comprises one or more biocompatible materials. The one or more biocompatible materials can be selected from the group consisting of: silicone, polyurethane, polyethylene terephthalate (PET), polyimide, polyether ether ketone (PEEK), platinum, nitinol, thermoplastic polymer resin, and thermoplastic elastomer. The one or more biocompatible materials of certain embodiments are configured to be sufficiently flexible such that the stimulation assembly 118 can be easily implanted into position. For example, the one or more biocompatible materials can comprise a metal helix that is configured to be both structurally robust and flexible. The one or more biocompatible materials of certain embodiments are configured to be easily cleaned of bacteria and/or tissue adhesion (e.g., during the second surgical procedure prior to repositioning the stimulation assembly 118) and/or to comprise one or more low fouling materials or coatings (e.g., materials or coatings that are configured to inhibit (e.g., reduce; prevent) an accumulation of unwanted tissue adhesion and/or a biofilm to the detriment of function of the tube 150, the stimulation assembly 118, and/or the apparatus 100).

In certain embodiments, the tube 150 comprises a plurality of biocompatible materials which are configured to provide selected functionalities. For example, the first end portion 318 of the tube 150 can comprise a hydrogel configured to respond to moisture by expanding in a radial direction, as schematically illustrated by FIG. 3E, while the remaining portions of the tube 150 can comprise one or more biocompatible materials configured to provide structural stability to the tube 150.

Figure 4A:
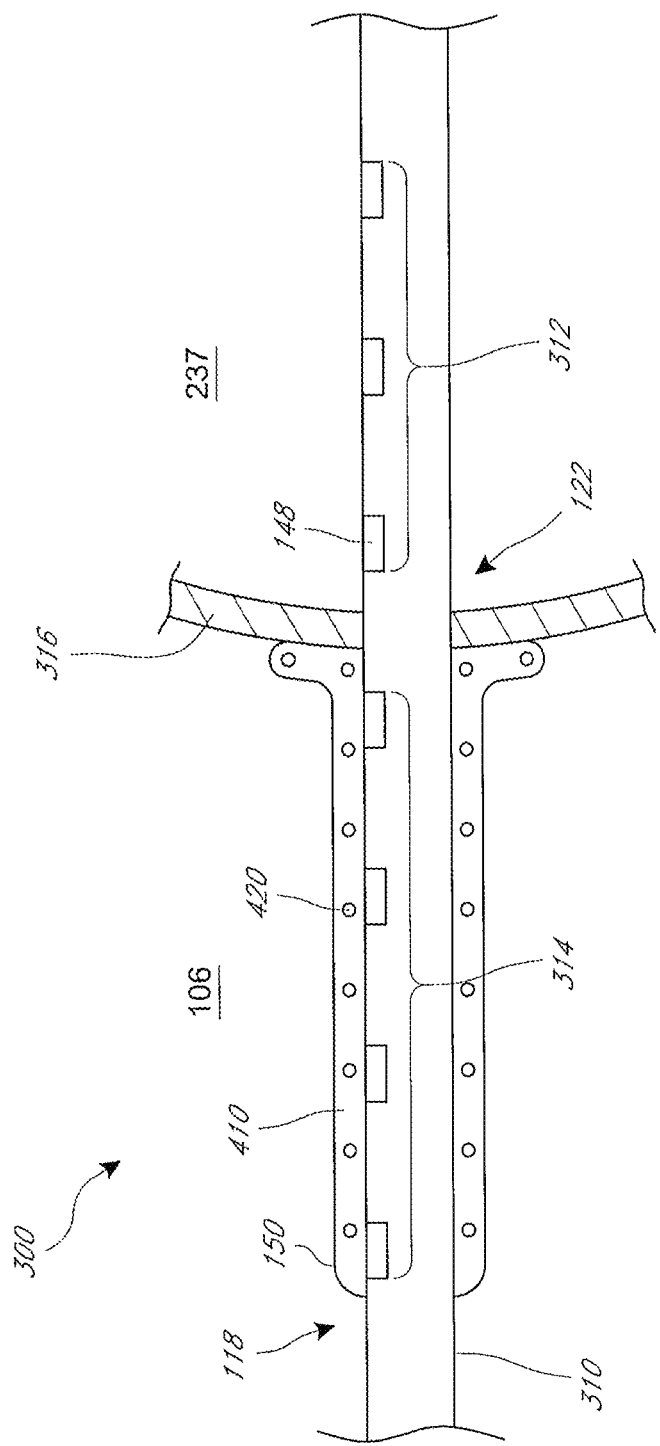
FIGS. 4A-4C schematically illustrate example tubes comprising at least one first biocompatible material and at least one second biocompatible material embedded within the at least one first biocompatible material in accordance with certain embodiments described herein.
Figure 4B:
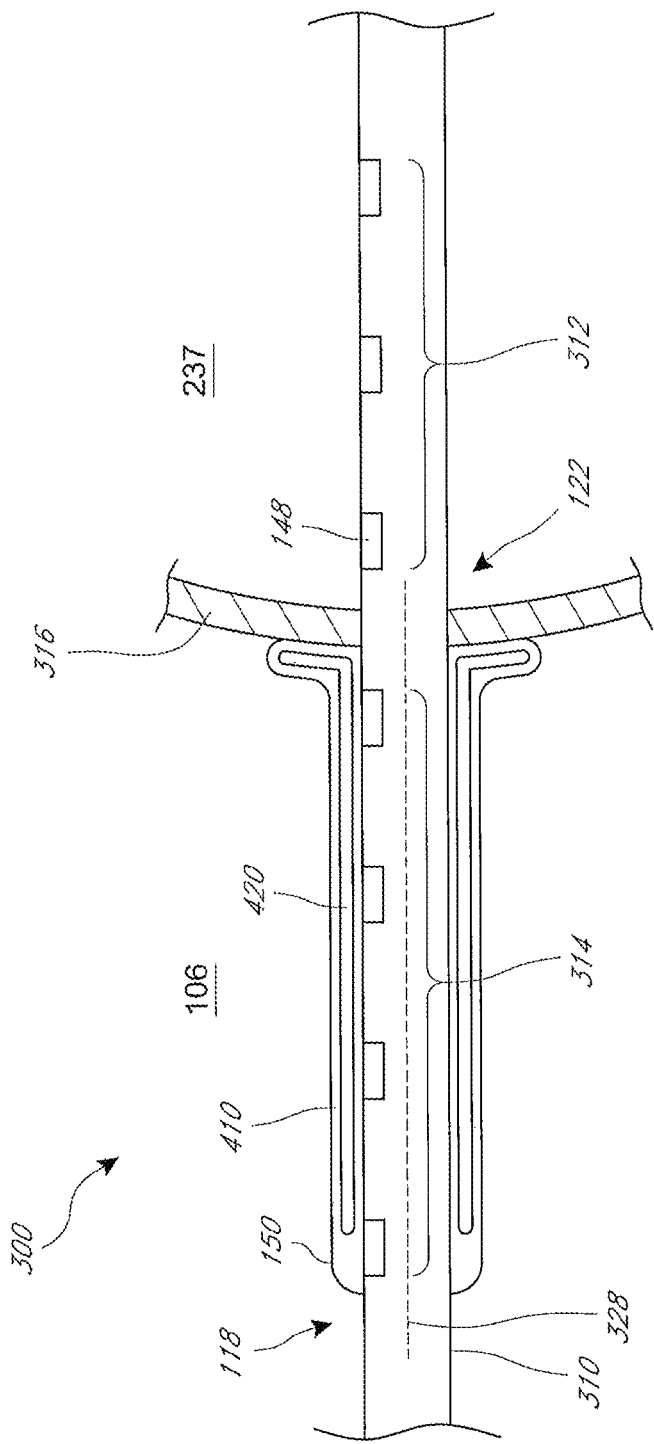
Figure 4C:
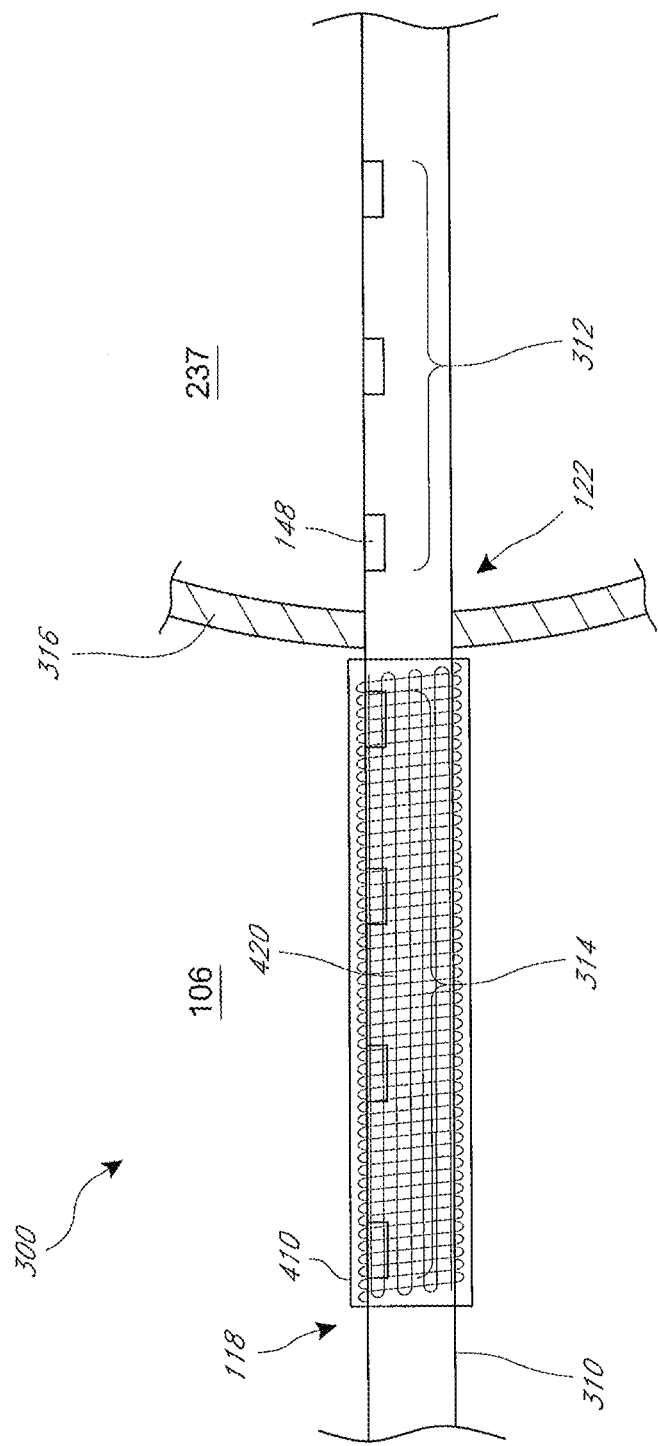

FIGS. 4A-4C schematically illustrate example tubes 150 comprising at least one first biocompatible material 410 and at least one second biocompatible material 420 embedded within the at least one first biocompatible material 410 in accordance with certain embodiments described herein. The at least one second biocompatible material 420 is configured to enhance a structural strength of the tube 150 (e.g., to reinforce the at least one first biocompatible material 410). For example, the at least one first biocompatible material 410 (e.g., silicone) can have a first structural strength and the at least one second biocompatible material 420 (e.g., PET; polyimide; platinum; nitinol) can have a second structural strength greater than the first structural strength. In certain such embodiments, the at least one second biocompatible material 420 advantageously structurally reinforces the tube 150 to be more robust to surgical exposure and/or more resilient to inadvertent cutting by a surgical tool (e.g., scalpel) as compared to a tube 150 that does not comprise the at least one second biocompatible material 420. The at least one first biocompatible material 410 and the at least one second biocompatible material 420 are configured to be sufficiently flexible such that the stimulation assembly 118 can be easily implanted into position.

As schematically illustrated by the cross-sectional view of an example tube 150 in FIG. 4A, at least some of the at least one second biocompatible material 420 can extend circumferentially around a portion of the stimulation assembly 118 (e.g., as a spiral that encircles the longitudinal axis 328 of the tube 150) and is embedded in the at least one first biocompatible material 410. As schematically illustrated by the cross-sectional view of an example tube 150 in FIG. 4B, at least some of the at least one second biocompatible material 420 can extend longitudinally along the portion of the stimulation assembly 118 (e.g., generally parallel to the longitudinal axis 328 of the tube 150) and is embedded in the at least one first biocompatible material 410. In certain embodiments, the at least one second biocompatible material 420 comprises a mesh wrapped around the portion of the stimulation assembly 118 (e.g., extending circumferentially around the longitudinal axis 328 and along the longitudinal axis 328), as schematically illustrated by FIG. 4C.

In certain embodiments, the tube 150 comprises at least one compound comprising at least one antimicrobial (e.g., antibacterial) agent, at least one anti-inflammatory agent, or both at least one antimicrobial agent and at least one anti-inflammatory agent. For example, the at least one antimicrobial agent can comprise silver particles and/or at least one antimicrobial drug (e.g., vancomycin; rifampicin; aminoglycosides; antimicrobial peptides; antifouling coatings; quorum sensing inhibitors), and the at least one anti-inflammatory agent can comprise at least one corticosteroid, at least one non-steroidal anti-inflammatory drug (NSAID), and/or at least one agent configured to inhibit (e.g., prevent) scarring or fibrosis on or around at least a portion of the tube 150. In certain embodiments, the tube 150 is configured to retain the at least one compound within or on the tube 150 (e.g., coated with the at least one compound), while in certain other embodiments, the tube 150 is configured to release the at least one compound from the tube 150 (e.g., to be eluted from the tube 150). For example, the tube 150 can comprise a biodegradable material containing the at least one compound and configured to release the at least one compound from the tube 150 as the biodegradable material degrades after the apparatus 100 has been implanted. For another example, the tube 150 can be configured to selectively release the at least one compound (e.g., at least one antimicrobial agent) from the tube 150 in response to at least one of a temperature of the middle ear region 106 and a moisture content of the middle ear region 106.

Figure 5A:
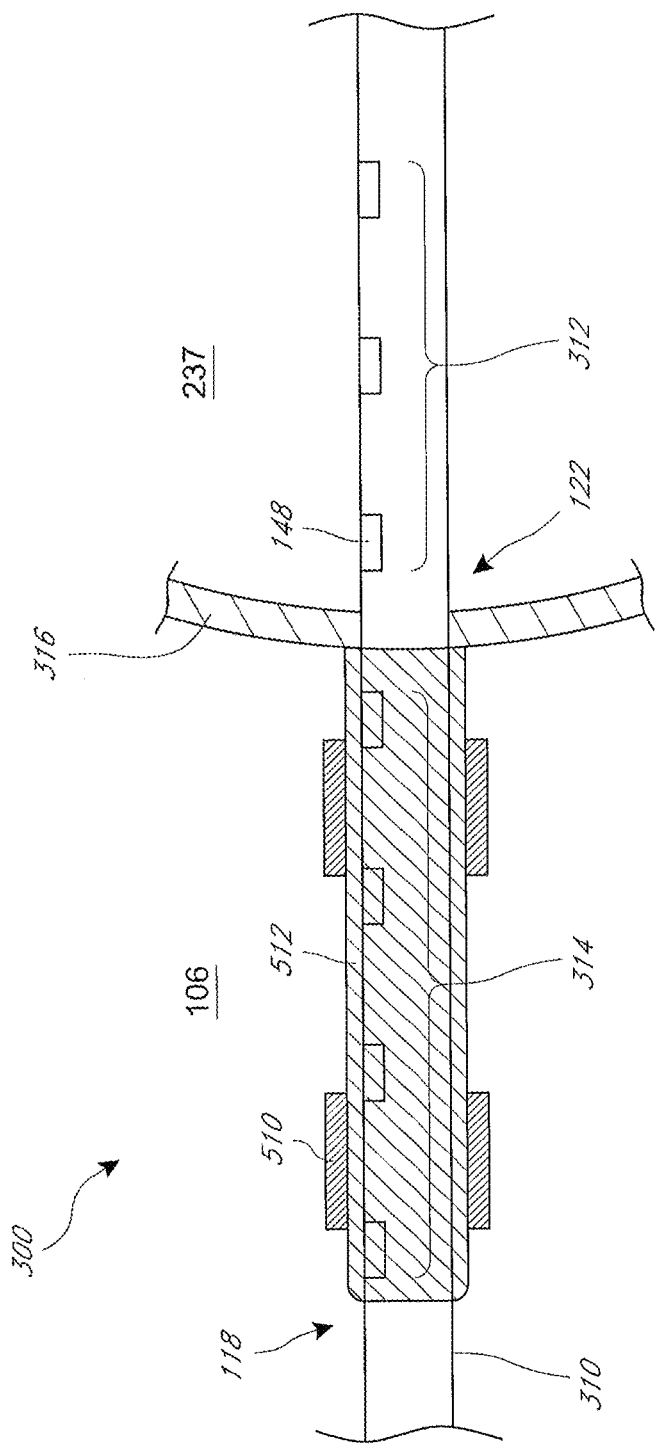
FIG. 5A schematically illustrates an example tube comprising one or more structures comprising at least one antimicrobial agent positioned on or within an outer surface of the tube, in accordance with certain embodiments described herein.
Figure 5B:
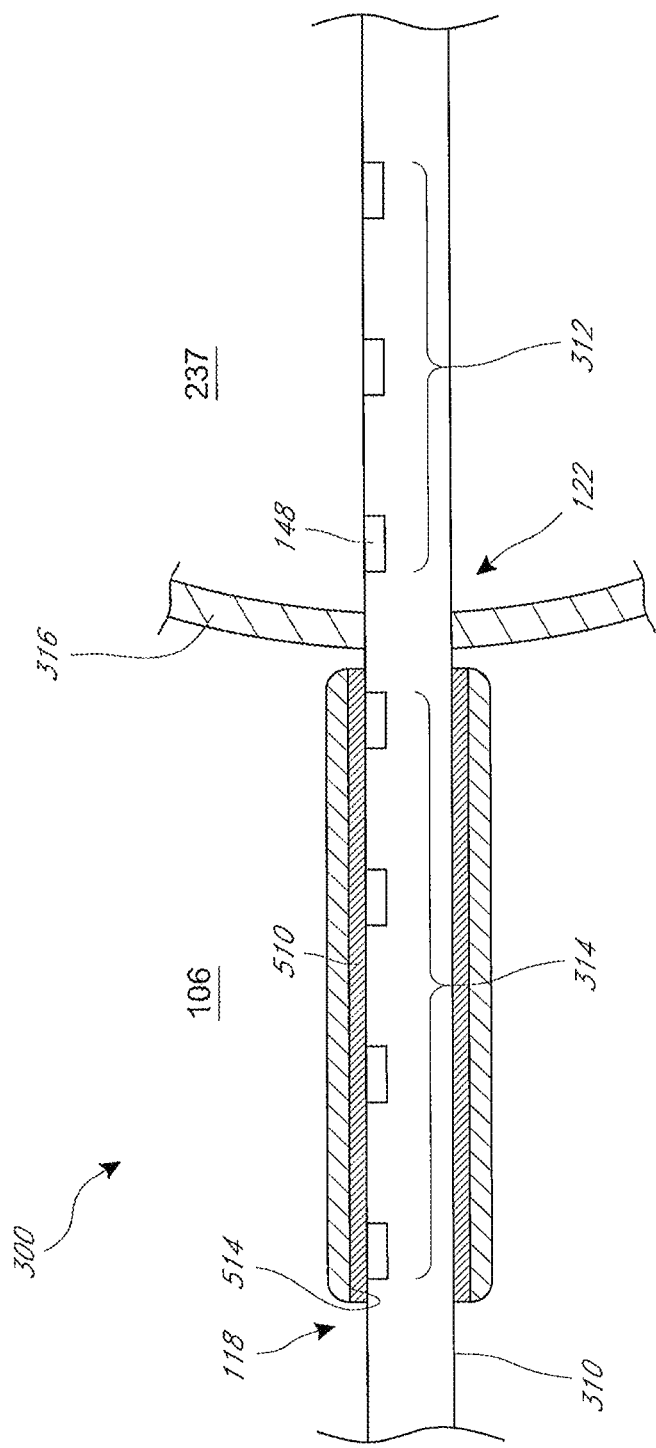
FIG. 5B schematically illustrates a cross-sectional view of an example tube comprising a bacteria-resistant barrier configured to protect the second set of the stimulation elements from bacterial contamination, in accordance with certain embodiments described herein.

FIG. 5A schematically illustrates an example tube 150 comprising one or more structures 510 comprising the at least one antimicrobial (e.g., antibacterial) agent positioned on or within an outer surface 512 of the tube 150. The one or more structures 510 can comprise one or more layers that extend circumferentially around at least a portion of the tube 150, longitudinally along at least a portion of the tube 150, or both circumferentially around and longitudinally along at least a portion of the tube 150. For example, the one or more layers can comprise a biodegradable material containing the at least one compound and configured to release the at least one compound as the biodegradable material degrades after the apparatus 100 has been implanted. FIG. 5B schematically illustrates a cross-sectional view of an example tube 150 comprising a bacteria-resistant barrier configured to protect the second set 314 of the stimulation elements 148 from bacterial contamination. For example, the structure 510 can comprise at least one layer comprising the at least one antibacterial agent, the at least one layer extending along at least a portion of an inner surface 514 of the tube 150 and configured to be in contact with the stimulation assembly 118 (e.g., extending circumferentially around the portion of the stimulation assembly 118 containing the second set 314 of the stimulation elements 148 and/or extending longitudinally along the portion of the stimulation assembly 118 containing the second set 314 of the stimulation elements 148).

In certain embodiments, the tube 150 comprises one or more portions (e.g., layers) configured to be removed (e.g., peeled off; torn; ripped; unwrapped) to facilitate removal of the tube 150 from the stimulation assembly 118. For example, the one or more portions (e.g., layers) can be configured to remain on the stimulation assembly 118 after the first surgical procedure (e.g., during which the apparatus 100 is implanted), and to be removed (e.g., peeled off; torn; ripped; unwrapped) during the second surgical procedure (e.g., during which the stimulation assembly 118 is repositioned by being inserted further into the cochlea 140). Removal of the one or more portions of certain embodiments also removes fibrosis tissue that has formed on the one or more portions during the time between the first surgical procedure and the second surgical procedure.

FIGS. 6A-6D schematically illustrate example tubes 150 having one or more portions configured to facilitate removal of the tube 150 from the stimulation assembly 118 in accordance with certain embodiments described herein. The example tube 150 of FIG. 6A comprises a plurality of layers (e.g., an outer layer 602 and an inner layer 604), each extending circumferentially around and longitudinally along the longitudinal axis 328 of the tube 150 (e.g., along the portion of the stimulation assembly 118 containing the second set 314 of the stimulation elements 148). The outer layer 602 substantially surrounds the inner layer 604 and is configured to be separated (e.g., peeled off; torn; ripped; unwrapped) and removed from the inner layer 604, and the inner layer 604 substantially surrounds the portion of the stimulation assembly 118 containing the second set 314 of the stimulation elements 148 and is configured to be separated (e.g., peeled off; torn; ripped; unwrapped) and removed from the stimulation assembly 118 after the outer layer 602 has been removed. For example, such layers can be formed using a multistage injection molding process comprising a first molding step to form the inner layer 604, treatment of the molded outer surface of the inner layer 604 to inhibit adhesion of the subsequently-formed layers, and a second molding step to form the outer layer 602 over the inner layer 604.

Figure 6A:
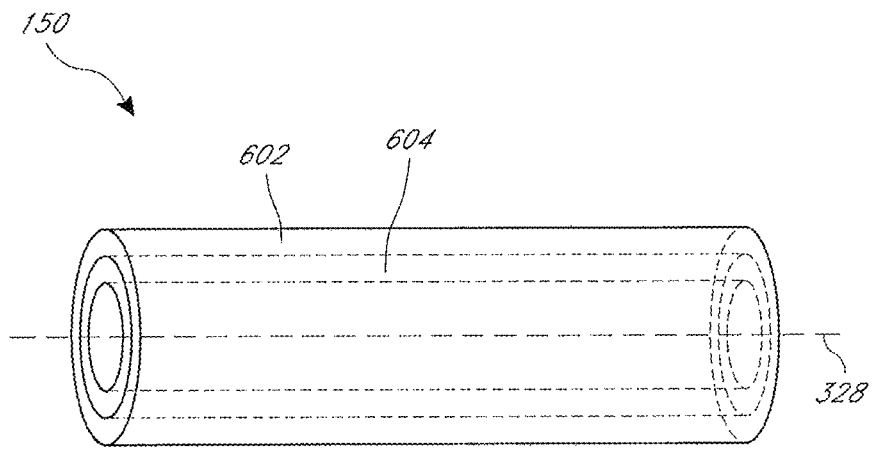
FIGS. 6A-6D schematically illustrate example tubes having one or more portions configured to facilitate removal of the tube from the stimulation assembly in accordance with certain embodiments described herein.
Figure 6B:
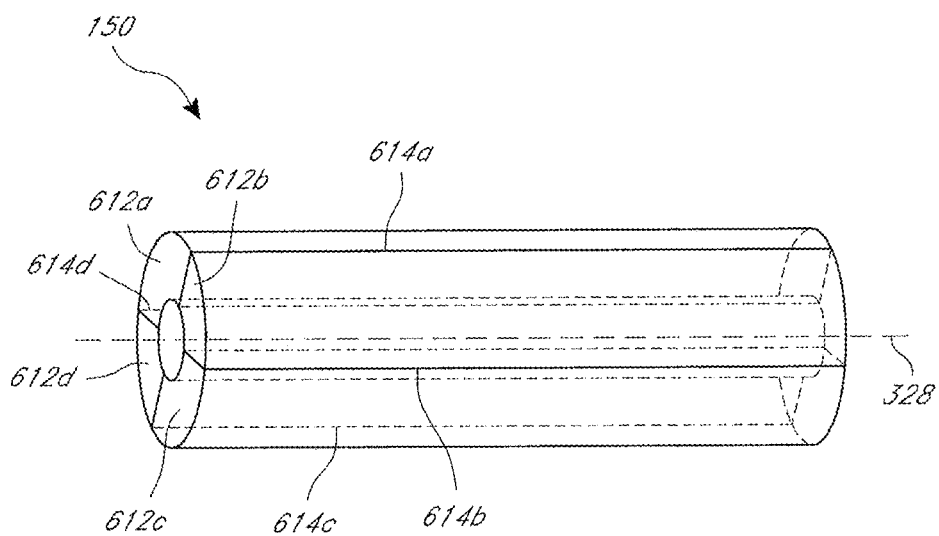
Figure 6C:
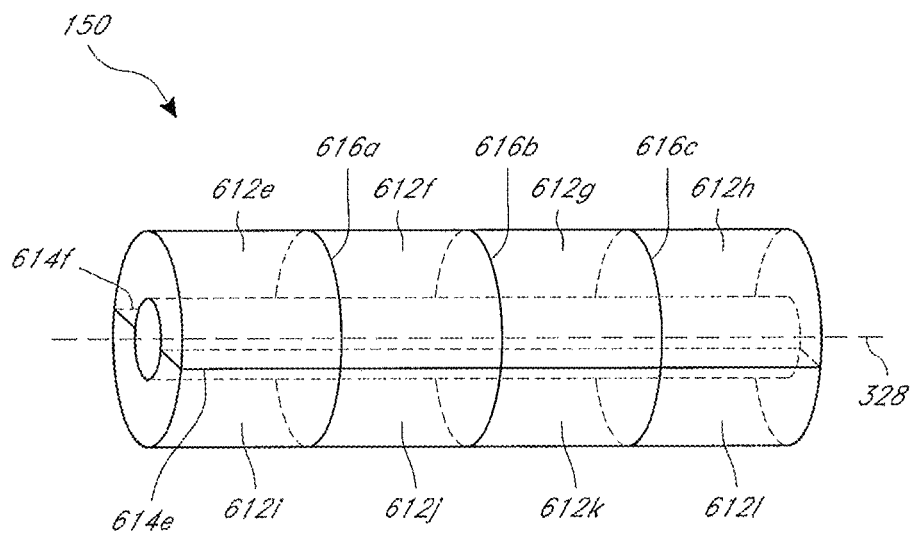
Figure 6D:
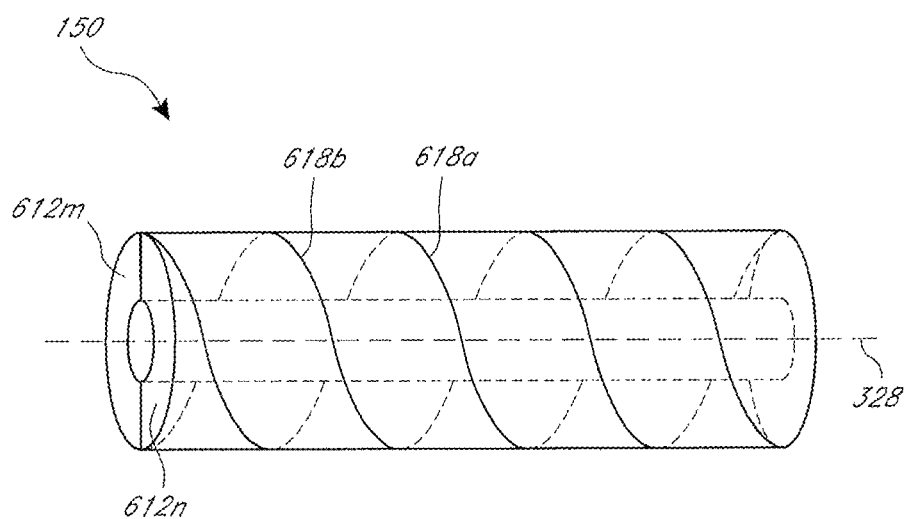

Each of the example tubes 150 of FIGS. 6B-6D comprises a plurality of portions 612 (e.g., layers) and a plurality of junctions (e.g., boundaries; seams) between adjacent portions 612, the junctions configured to facilitate the adjacent portions 612 to be separated (e.g., peeled; torn; ripped; unwrapped) and removed from one another. For example, the tube 150 of FIG. 6B comprises four portions 612a-d extending longitudinally along the tube 150 and having four junctions 614a-d that also extend longitudinally along the tube 150. The junction 614a is between the two portions 612a, 612b, the junction 614b is between the two portions 612b, 612c, the junction 614c is between the two portions 612c, 612d, and the junction 614d is between the two portions 612d, 612a. Each of the junctions 614a-d is configured to facilitate the two corresponding portions 612a-d to be separated from one another, thereby allowing the tube 150 to be removed from the stimulation assembly 118. For example, by pulling on the portion 612b with sufficient force to tear the two junctions 614a-b, the portion 612b can be separated from the adjacent portions 612a, 612c (e.g., analogous to the peeling of a banana) and removed from the stimulation assembly 118. The junctions 614a-d can comprise weakened structures (e.g., seams; scored lines) that are configured to remain intact after the first surgical procedure and to be easily separated (e.g., peeled from; torn; ripped; unwrapped) during the second surgical procedure. For example, such weakened structures can be formed using a multistage injection molding process comprising multiple molding steps to separately form each of the portions 612, with intervening treatments of the molded surfaces of the previously-formed portions to inhibit adhesion of the subsequently-formed portions.

For another example, the tube 150 of FIG. 6C comprises eight portions 612e-1, each extending longitudinally along the longitudinal axis 328 of the tube 150 and having two junctions 614e-f extending longitudinally along the longitudinal axis 328 and three junctions 616a-c extending circumferentially around the longitudinal axis 328. Each of the junctions 614e-f, 616a-c is configured to facilitate two adjacent portions 612e-1 to be separated from one another, thereby allowing the tube 150 to be removed from the stimulation assembly 118. For still another example, the tube 150 of FIG. 6D comprises two portions 612m-n, each extending longitudinally along and circumferentially around the longitudinal axis 328 (e.g., as a spiral) and having two junctions 618a-b extending longitudinally along and circumferentially around the longitudinal axis 328 (e.g., as a spiral). Each of the junctions 618a-b is configured to facilitate the two portions 612m-n to be separated from one another, thereby allowing the tube 150 to be removed from the stimulation assembly 118.

Figure 7A:
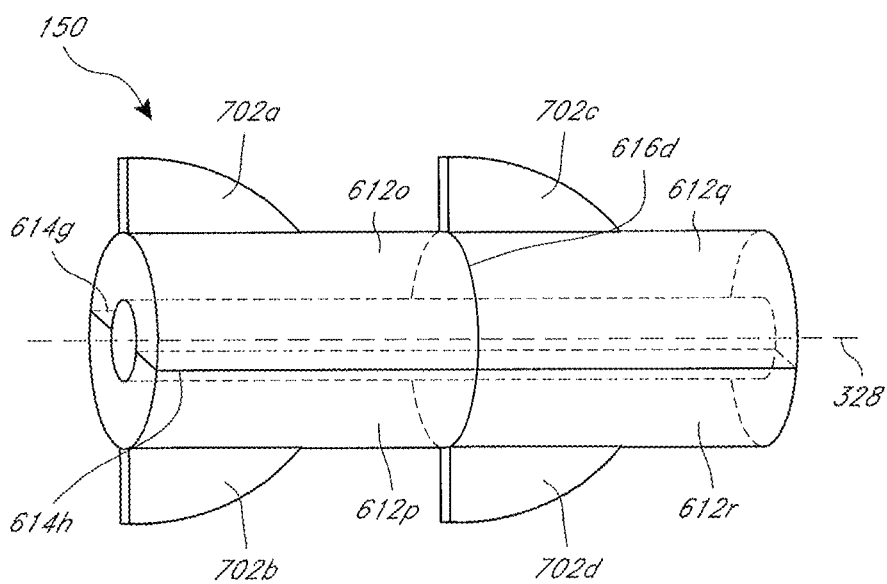
FIGS. 7A and 7B schematically illustrate example tubes having one or more protrusions configured to facilitate manipulation of the stimulation assembly in accordance with certain embodiments described herein.
Figure 7B:
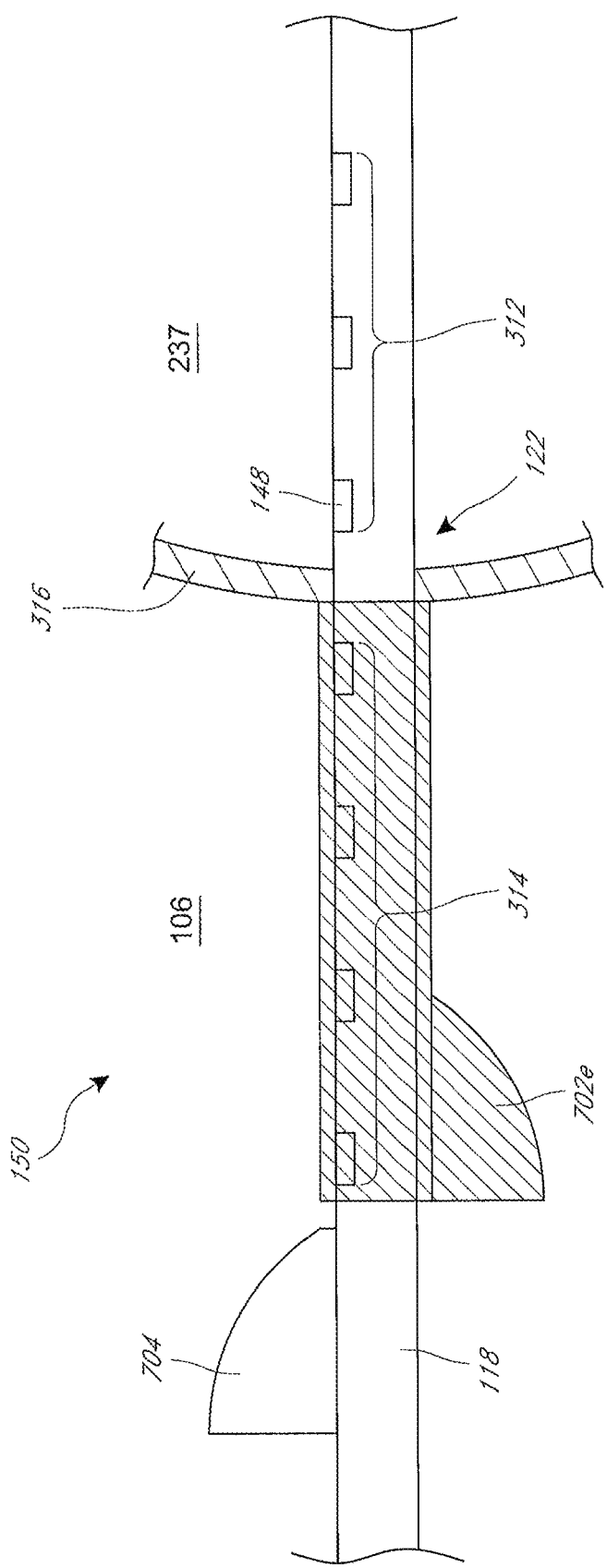

FIGS. 7A and 7B schematically illustrate example tubes 150 having one or more protrusions 702 (e.g., wings; tabs; handles; grips) configured to facilitate manipulation of the stimulation assembly 118 (e.g., during at least one of the first surgical procedure and the second surgical procedure) in accordance with certain embodiments described herein. The example tube 150 of FIG. 7A comprises four portions 612o-r extending longitudinally along the longitudinal axis 328, having two junctions 614g-h that extend longitudinally along the longitudinal axis 328, and having one junction 616d extending circumferentially around the longitudinal axis 328. The tube 150 further comprises four protrusions 702a-d, each protrusion 702a-d part of a corresponding portion 612o-r. Each of the protrusions 702a-d is configured to facilitate manipulation of the stimulation assembly 118 during at least one of the first surgical procedure (e.g., to be gripped by a surgical tool for positioning the stimulation assembly 118 during implantation of the apparatus 100) and the second surgical procedure (e.g., to be gripped by a surgical tool for at least partially withdrawing the stimulation assembly 118 from the cochlea 140 during the repositioning of the stimulation assembly 118). In certain embodiments, each of the protrusions 702a-d is further configured to facilitate removal of the tube 150 from the stimulation assembly 118 during the second surgical procedure (e.g., to be gripped by a surgical tool for separating the corresponding portion 612o-r from the other portions).

The example tube 150 of FIG. 7B comprises at least one first protrusion 702e and the stimulation assembly 118 comprises at least one second protrusion 704 (e.g., wing; tab; handle; grip). The at least one first protrusion 702e and the at least one second protrusion 704 are configured to facilitate manipulation of the stimulation assembly 118 during the first surgical procedure (e.g., to be gripped by a surgical tool for positioning the stimulation assembly 118 during implantation of the apparatus 100). The at least one second protrusion 704 is further configured to facilitate manipulation of the stimulation assembly 118 during the second surgical procedure (e.g., to be gripped by a surgical tool during the repositioning of the stimulation assembly 118) after the tube 150 has been removed from the stimulation assembly 150. In certain such embodiments, the at least one first protrusion 702e is further configured to facilitate removal of the tube 150 from the stimulation assembly 118 during the second surgical procedure (e.g., to be gripped by a surgical tool for peeling, tearing, ripping, and/or unwrapping the tube 150 from the stimulation assembly 118).

Figure 8A:
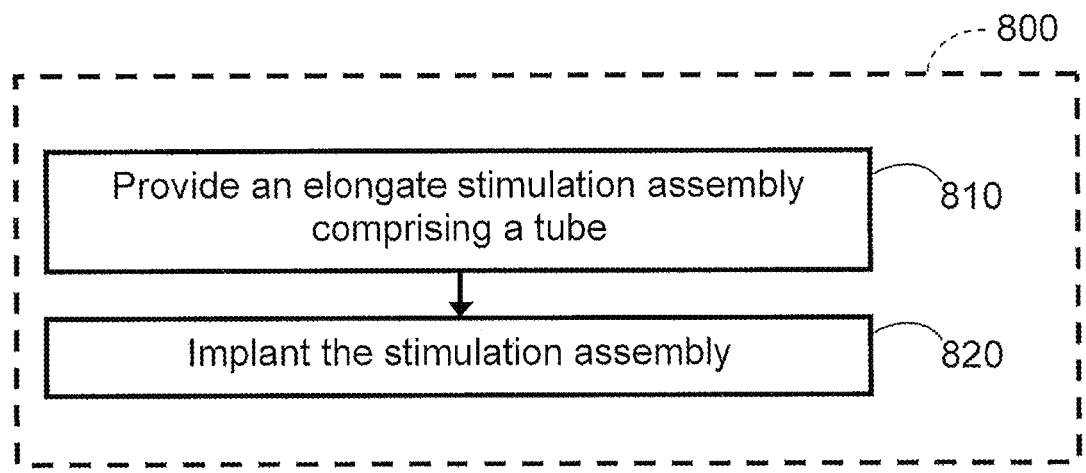
FIGS. 8A and 8B are flow diagrams of an example method in accordance with certain embodiments described herein.
Figure 8B:
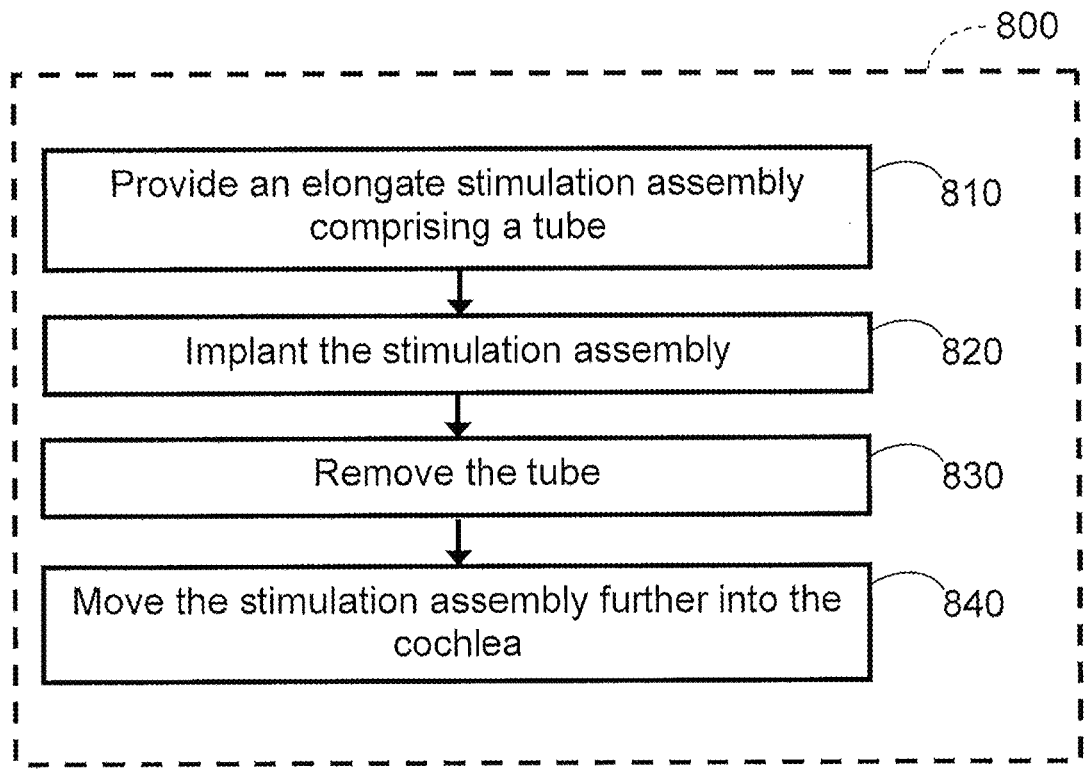
Figure 8C:
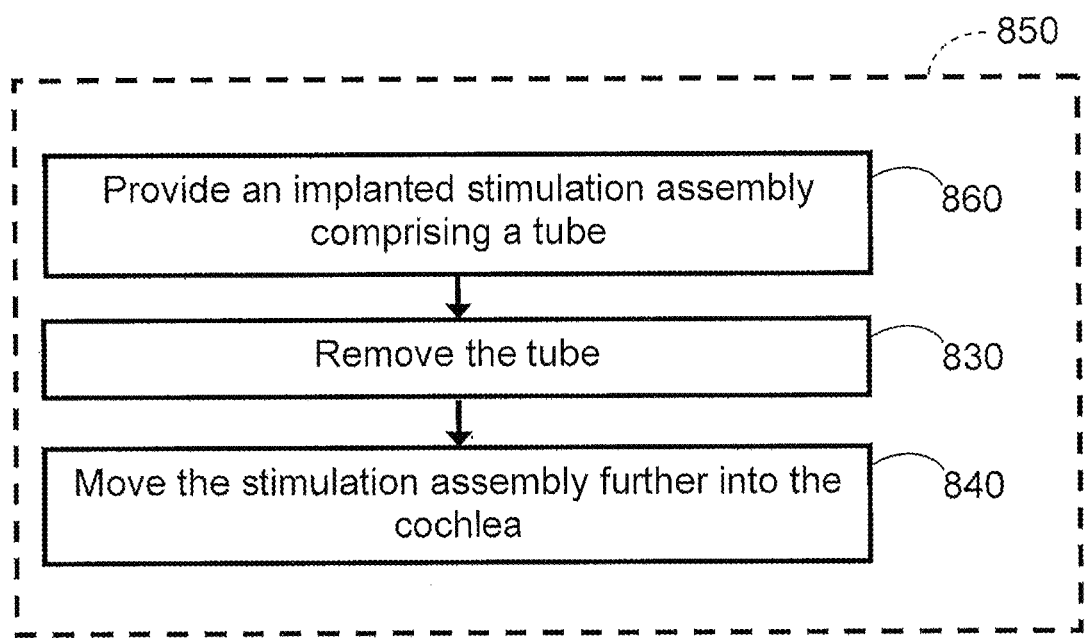
FIG. 8C is a flow diagram of another example method in accordance with certain embodiments described herein.

FIGS. 8A and 8B are flow diagrams of an example method 800 in accordance with certain embodiments described herein, and FIG. 8C is a flow diagram of another example method 850 in accordance with certain embodiments described herein. While the example methods 800, 850 are described herein by referring to the example apparatus 100 of FIGS. 1-7, the methods 800, 850 can be performed using other systems, apparatuses, and/or devices as well.

In an operational block 810, the method 800 comprises providing an elongate stimulation assembly 118 comprising a plurality of stimulation elements 148 configured to stimulate spiral ganglion cells of a cochlea 140 of a recipient. For example, the plurality of stimulation elements 148 can comprise a first set 312 of stimulation elements and a second set of stimulation elements 314. The stimulation assembly 118 further comprises a tube 150 covering some of the stimulation elements 148 but fewer than all of the stimulation elements 148. For example, the tube 150 can cover the second set 314 of stimulation elements 148 while not covering the first set 312 of stimulation elements 148. The tube 150 is configured to be removed from the stimulation assembly 118.

In an operational block 820, the method 800 further comprises implanting the stimulation assembly 118 such that the tube 150 is positioned externally to the cochlea 140 (e.g., during a first surgical procedure, inserting the stimulation assembly 118 through an opening in the cochlea 140 and forming a seal between the tube 150 and the cochlea 140). For example, the stimulation assembly 118 can be implanted such that the first set 312 of stimulation elements 148 are positioned within the cochlea 140 and the second set 314 of stimulation elements 148 and the tube 150 are positioned within a middle ear region 106 of the recipient externally to the cochlea 140. In certain such embodiments, the stimulation assembly 118 is positioned within the cochlea 140 so as to allow residual hearing in a first frequency range using the cochlea 140 while the stimulation assembly 118 is configured to assist hearing in a second frequency range using the cochlea 140, the second frequency range higher than the first frequency range.

In certain embodiments, the method 800 further comprises removing the tube 150 from the stimulation assembly 118 in an operational block 830 and moving the stimulation assembly 118 further into the cochlea 140 in an operational block 840, as shown in FIG. 8B. For example, the tube 150 can be removed during a second surgical procedure that can be less invasive than the first surgical procedure, and the stimulation assembly 118 can be moved further into the cochlea 140 such that both the first set 312 of stimulation elements 148 and the second set 314 of stimulation elements 148 are positioned within the cochlea 140 (e.g., such that the stimulation assembly 118 is configured to assist hearing using the cochlea 140 in the first frequency range and the second frequency range).

In certain embodiments, the method 850 comprises providing an implanted stimulation assembly 118 comprising a tube 150 in an operational block 860. For example, the implanted stimulation assembly 118 can be previously implanted during a first surgical procedure (e.g., the operational block 860 is performed after the operational blocks 810 and 820 of FIG. 8A had been performed). The method 850 further comprises removing the tube 150 from the stimulation assembly 118 in the operational block 830 and moving the stimulation assembly 118 further into the cochlea 140 in the operational block 840, as disclosed herein with regard to the example method 800 of FIG. 8B.

In certain embodiments, the first surgical procedure and the second surgical procedure are performed by the same health professional (e.g., surgeon), while in certain other embodiments, the first surgical procedure is performed by a first health professional (e.g., a first surgeon) and the second surgical procedure is performed by a second health professional (e.g., a second surgeon) different from the first health professional.

It is to be appreciated that the embodiments disclosed herein are not mutually exclusive and may be combined with one another in various arrangements. In addition, although the disclosed methods and apparatuses have largely been described in the context of conventional cochlear implants, various embodiments described herein can be incorporated in a variety of other suitable devices, methods, and contexts, including but not limited to totally implantable cochlear implants ("TICIs") and/or mostly implantable cochlear implants ("MICIs"). For example, TICIs can utilize a battery and a microphone which are both implanted within the body of the recipient (e.g., as components of either a monolithic system or as a collection of modules coupled together) that are capable of operating, at least for a period of time, without the need for an external device and without the need for any transcutaneous transmission of signals. For another example, MICIs can utilize a battery implanted within the body of the recipient, all or some of the sound processing can be performed by the implant, and a smaller (or very small) external processor can contain the microphone and the capability to wirelessly transmit information to the implant via RF signals (as done in current cochlear implant systems) or any other wireless data and/or audio transmission scheme. More generally, as can be appreciated, certain embodiments described herein can be used in a variety of implantable medical device contexts that can benefit from progressive insertion.

The invention described and claimed herein is not to be limited in scope by the specific example embodiments herein disclosed, since these embodiments are intended as illustrations, and not limitations, of several aspects of the invention. Any equivalent embodiments are intended to be within the scope of this invention. Indeed, various modifications of the invention in form and detail, in addition to those shown and described herein, will become apparent to those skilled in the art from the foregoing description. Such modifications are also intended to fall within the scope of the claims. The breadth and scope of the invention should not be limited by any of the example embodiments disclosed herein, but should be defined only in accordance with the claims and their equivalents.

Certain Embodiments

Certain embodiments are listed below. The following embodiments are presented for explanatory and illustrative purposes only. It will be appreciated that the foregoing description is not limited to the following embodiments.

Embodiment 1: An apparatus comprising a stimulation assembly comprising an elongate body and a plurality of stimulation elements longitudinally spaced from one another along a portion of the elongate body. The stimulation assembly comprises a first set of the stimulation elements and a second set of the stimulation elements. The apparatus further comprises a tube over the second set of the stimulation elements. The tube is configured to be removed from the stimulation assembly.

Embodiment 2: The apparatus of Embodiment 1, wherein the stimulation assembly is configured to be implanted such that the first set of the stimulation elements is within the cochlea and the second set of the stimulation elements is outside the cochlea. The first set of the stimulation elements are configured to provide stimulation signals to the cochlea. The tube is configured to be removed from the stimulation assembly while the first set of the stimulation elements is within the cochlea and the second set of the stimulation elements is outside the cochlea.

Embodiment 3: The apparatus of Embodiment 1, wherein the stimulation assembly comprises an elongate electrode array and the plurality of stimulation elements comprises a plurality of electrodes.

Embodiment 4: The apparatus of any of Embodiments 1 to 3, wherein the tube comprises one or more biocompatible materials selected from the group consisting of: silicone, polyurethane, polyethylene terephthalate (PET), polyimide, platinum, nitinol, polyether ether ketone (PEEK), thermoplastic polymer resin, and thermoplastic elastomer.

Embodiment 5: The apparatus of any of Embodiments 1 to 4, wherein the tube comprises at least one first biocompatible material and at least one second biocompatible material embedded within the at least one first biocompatible material, the at least one second biocompatible material configured to enhance a structural strength of the tube.

Embodiment 6: The apparatus of Embodiment 5, wherein the at least one first biocompatible material comprises silicone and the at least one second biocompatible material comprises polyethylene terephthalate (PET), polyimide, platinum, or nitinol.

Embodiment 7: The apparatus of Embodiment 5, wherein at least some of the at least one second biocompatible material extends circumferentially around a portion of the stimulation assembly.

Embodiment 8: The apparatus of Embodiment 5, wherein at least some of the at least one second biocompatible material extends longitudinally along a portion of the stimulation assembly.

Embodiment 9: The apparatus of Embodiment 5, wherein the at least one second biocompatible material comprises a mesh wrapped around a portion of the stimulation assembly.

Embodiment 10: The apparatus of any of Embodiments 1 to 9, wherein the tube comprises one or more layers configured to be peeled off to facilitate removal of the tube from the stimulation assembly.

Embodiment 11: The apparatus of any of Embodiments 1 to 10, wherein the tube comprises one or more portions configured to be torn to facilitate removal of the tube from the stimulation assembly.

Embodiment 12: The apparatus of any of Embodiments 1 to 11, wherein the tube comprises one or more protrusions configured to facilitate manipulation of the stimulation assembly.

Embodiment 13: The apparatus of Embodiment 12, wherein the one or more protrusions are further configured to facilitate removal of the tube from the stimulation assembly.

Embodiment 14: The apparatus of any of Embodiments 1 to 13, wherein the tube has a first end portion configured to contact an outer surface of the cochlea and to form a bacteria-resistant barrier configured to prevent bacteria from entering the cochlea.

Embodiment 15: The apparatus of Embodiment 14, wherein the first end portion is configured to expand in a radial direction along the outer surface of the cochlea.

Embodiment 16: The apparatus of any of Embodiments 1 to 15, wherein the tube comprises a bacteria-resistant barrier configured to protect the second set of stimulation elements from bacterial contamination.

Embodiment 17: The apparatus of any of Embodiments 1 to 16, wherein the tube comprises at least one compound comprising at least one antimicrobial agent, at least one anti-inflammatory agent, or both at least one antimicrobial agent and at least one anti-inflammatory agent.

Embodiment 18: The apparatus of Embodiment 17, wherein the at least one antimicrobial agent comprises silver particles or at least one drug.

Embodiment 19: The apparatus of Embodiment 17, wherein the at least one anti-inflammatory agent comprises at least one corticosteroid, at least one non-steroidal anti-inflammatory drug (NSAID), or at least one agent configured to inhibit scarring or fibrosis on or around at least a portion of the tube.

Embodiment 20: The apparatus of any of Embodiments 17 to 19, wherein the tube is configured to release the at least one compound from the tube.

Embodiment 21: The apparatus of Embodiment 20, wherein the tube is configured to selectively release the at least one compound from the tube in response to at least one of a temperature of a middle ear region of the recipient and a moisture content of the middle ear region of the recipient.

Embodiment 22: An apparatus comprising a stimulation assembly comprising a plurality of stimulation elements configured to provide stimulation signals to a cochlea of a recipient. The plurality of stimulation elements comprises a first set of stimulation elements configured to be positioned within the cochlea during a first surgical procedure and a second set of stimulation elements configured to be positioned within a middle ear region of the recipient externally to the cochlea during the first surgical procedure. The apparatus further comprises a tube over the second set of stimulation elements. The tube is configured to remain within the middle ear region after the first surgical procedure and to be removed from the stimulation assembly during a second surgical procedure.

Embodiment 23: The apparatus of Embodiment 22, wherein the stimulation assembly is configured to be inserted into the cochlea to a first angular insertion depth during the first surgical procedure and to be further inserted into the cochlea to a second angular insertion depth during the second surgical procedure, the second angular insertion depth greater than the first angular insertion depth.

Embodiment 24: The apparatus of Embodiment 22 or Embodiment 23, wherein the tube comprises one or more layers configured to remain on the stimulation assembly after the first surgical procedure and to be peeled off during the second surgical procedure.

Embodiment 25: The apparatus of any of Embodiments 22 to 24, wherein the tube comprises one or more portions configured to remain intact after the first surgical procedure and to be torn during the second surgical procedure.

Embodiment 26: The apparatus of any of Embodiments 22 to 25, wherein the tube comprises one or more protrusions configured to facilitate manipulation of the stimulation assembly during at least one of the first surgical procedure and the second surgical procedure.

Embodiment 27: The apparatus of Embodiment 26, wherein the one or more protrusions are configured to facilitate removal of the tube from the stimulation assembly during the second surgical procedure.

Embodiment 28: The apparatus of Embodiment 26, wherein the one or more protrusions comprises at least one first protrusion and the stimulation assembly comprises at least one second protrusion, the at least one first protrusion and the at least one second protrusion configured to facilitate manipulation of the stimulation assembly during the first surgical procedure, the at least one second protrusion further configured to facilitate manipulation of the stimulation assembly during the second surgical procedure after the tube has been removed from the stimulation assembly.

Embodiment 29: The apparatus of Embodiment 28, wherein the at least one first protrusion is further configured to facilitate removal of the tube from the stimulation assembly during the second surgical procedure.

Embodiment 30: A method comprising providing an elongate stimulation assembly comprising a plurality of stimulation elements configured to stimulate spiral ganglion cells of a cochlea of a recipient. The plurality of stimulation elements comprises a first set of stimulation elements and a second set of stimulation elements. The assembly further comprising a tube covering the second set of stimulation elements and not covering the first set of stimulation elements. The tube is configured to be removed from the stimulation assembly. The method further comprises implanting the stimulation assembly such that the first set of stimulation elements are positioned within the cochlea and the second set of stimulation elements and the tube are positioned within a middle ear region of the recipient externally to the cochlea.

Embodiment 31: The method of Embodiment 30, further comprising removing the tube from the stimulation assembly and moving the stimulation assembly further into the cochlea such that both the first set of stimulation elements and the second set of stimulation elements are positioned within the cochlea.

Embodiment 32: The method of Embodiment 31, wherein removing the tube comprises peeling, tearing, ripping, or unwrapping the tube from the stimulation assembly.

Embodiment 33: The method of any of Embodiments 30 to 32, wherein the tube comprises at least one antimicrobial agent and the method further comprises releasing the at least one antimicrobial agent from the tube in response to temperature within the middle ear region or moisture within the middle ear region.

Embodiment 34: The method of any of Embodiments 30 to 33, wherein implanting the stimulation assembly comprises inserting the stimulation assembly through an opening in the cochlea and positioning the stimulation assembly such that a first end of the tube is proximal to the opening.

Embodiment 35: The method of Embodiment 34, wherein implanting the stimulation assembly further comprises forming a seal between the tube and the cochlea, the seal configured to prevent bacteria from entering the cochlea through the opening.

Embodiment 36: The method of Embodiment 34 or Embodiment 35, wherein the opening comprises a cochleostomy or a round window of the cochlea.

Embodiment 37: A method comprising providing an elongate stimulation assembly comprising a plurality of stimulation elements configured to stimulate spiral ganglion cells of a cochlea of a recipient and a tube covering some of the stimulation elements but fewer than all of the stimulation elements. The tube is configured to be removed from the stimulation assembly. The method further comprises implanting the stimulation assembly within the cochlea of a recipient such that the tube is positioned externally to the cochlea. The stimulation assembly is positioned within the cochlea so as to allow residual hearing in a first frequency range using the cochlea while the stimulation assembly is configured to assist hearing in a second frequency range using the cochlea. The second frequency range is higher than the first frequency range.

Embodiment 38: The method of Embodiment 37, further comprising removing the tube from the stimulation assembly and moving the stimulation assembly further into the cochlea such that the stimulation assembly is configured to assist hearing using the cochlea in the first frequency range and the second frequency range.

Embodiment 39: The method of Embodiment 37 or Embodiment 38, wherein implanting the stimulation assembly comprises, during a first surgical procedure, inserting the stimulation assembly through an opening in the cochlea and forming a seal between the tube and the cochlea, the seal configured to prevent bacteria from entering the cochlea through the opening.

Embodiment 40: The method of Embodiment 39, wherein removing the tube from the stimulation assembly and moving the stimulation assembly further into the cochlea are performed during a second surgical procedure, the second surgical procedure less invasive than the first surgical procedure.

Embodiment 41: A method comprising providing an implanted stimulation assembly comprising a first set of stimulation elements within a cochlea of a recipient, a second set of stimulation elements external to the cochlea, and a tube covering the second set of stimulation elements. The tube is configured to be removed from the stimulation assembly. The method further comprises removing the tube from the stimulation assembly. The method further comprises moving the stimulation assembly further into the cochlea such that both the first set of stimulation elements and the second set of stimulation elements are positioned within the cochlea.

Embodiment 42: The method of Embodiment 41, wherein removing the tube comprises peeling, tearing, ripping, or unwrapping the tube from the stimulation assembly.

Embodiment 43: The method of Embodiment 41, wherein the implanted stimulation assembly is positioned within the cochlea so as to allow residual hearing in a first frequency range using the cochlea and to assist hearing in a second frequency range higher than the first frequency range, and moving the stimulation assembly further into the cochlea comprises repositioning the stimulation assembly such that the stimulation assembly is configured to assist hearing in both the first frequency range and the second frequency range.

Embodiment 44: The method of Embodiment 41, wherein the implanted stimulation assembly had been previously implanted during a first surgical procedure and removing the tube from the stimulation assembly and moving the stimulation assembly further into the cochlea are performed during a second surgical procedure less invasive than the first surgical procedure.

What is claimed is:

1. An apparatus comprising:
   a stimulation assembly comprising an elongate body and a plurality of stimulation elements longitudinally spaced from one another along a portion of the elongate body, the stimulation assembly comprising a first set of the stimulation elements and a second set of the stimulation elements, the stimulation assembly configured to be implanted during an implantation procedure in a recipient with the first set of the stimulation elements within a cochlea and the second set of the stimulation elements outside the cochlea; and
   a tube over the second set of the stimulation elements, the tube configured to remain implanted after the implantation procedure and while the first set of stimulation elements allows residual hearing in a first frequency range using the cochlea and assists hearing in a second frequency range using the cochlea, the second frequency range higher than the first frequency range, the tube configured to be removed from the stimulation assembly during a subsequent procedure after the implantation procedure and after the first set of the stimulation elements allows the residual hearing in the first frequency range and assists the hearing in the second frequency range, the tube comprising an inner layer portion over the second set of the stimulation elements and an outer layer portion over the inner layer portion, the outer layer portion configured to be removed from the inner layer portion and the inner layer portion configured to be removed from the second set of the stimulation elements such that the stimulation assembly remains implanted within the cochlea and the second set of stimulation elements is configured to be inserted within the cochlea.

2. The apparatus of claim 1, wherein the tube is configured to be removed from the stimulation assembly during the subsequent procedure while the first set of the stimulation elements is within the cochlea and the second set of the stimulation elements is outside the cochlea.

3. The apparatus of claim 1, wherein the stimulation assembly comprises an elongate electrode array and the plurality of stimulation elements comprises a plurality of electrodes.

4. The apparatus of claim 1, wherein the tube comprises one or more biocompatible materials selected from the group consisting of: silicone, polyurethane, polyethylene terephthalate (PET), polyimide, platinum, nitinol, polyether ether ketone (PEEK), thermoplastic polymer resin, and thermoplastic elastomer.

5. The apparatus of claim 1, wherein the tube comprises at least one first biocompatible material and at least one second biocompatible material embedded within the at least one first biocompatible material, the at least one second biocompatible material configured to enhance a structural strength of the tube.

6. The apparatus of claim 5, wherein the at least one first biocompatible material comprises silicone and the at least one second biocompatible material comprises polyethylene terephthalate (PET), polyimide, platinum, or nitinol.

7. The apparatus of claim 5, wherein at least some of the at least one second biocompatible material extends circumferentially around a portion of the stimulation assembly, extends longitudinally along a portion of the stimulation assembly, and/or comprises a mesh wrapped around a portion of the stimulation assembly.

8. The apparatus of claim 1, wherein the inner layer portion and the outer layer portion extend circumferentially around and longitudinally along a longitudinal axis of the tube and are configured to be unwrapped from the stimulation assembly.

9. The apparatus of claim 1, wherein the inner layer portion are configured to be removed from the stimulation assembly after the outer layer portion is removed.

10. The apparatus of claim 1, wherein the tube comprises one or more protrusions configured to facilitate manipulation of the stimulation assembly and/or to facilitate removal of the tube from the stimulation assembly.

11. The apparatus of claim 1, wherein the tube has a first end portion configured to contact an outer surface of the cochlea and to form a bacteria-resistant barrier configured to prevent bacteria from entering the cochlea.

12. The apparatus of claim 11, wherein the first end portion is configured to expand in a radial direction along the outer surface of the cochlea.

13. The apparatus of claim 1, wherein the tube comprises a bacteria-resistant barrier configured to protect the second set of stimulation elements from bacterial contamination.

14. The apparatus of claim 1, wherein the tube comprises at least one compound comprising at least one antimicrobial agent, at least one anti-inflammatory agent, or both at least one antimicrobial agent and at least one anti-inflammatory agent.

15. The apparatus of claim 14, wherein the at least one antimicrobial agent comprises silver particles, at least one drug, at least one corticosteroid, at least one non-steroidal anti-inflammatory drug (NSAID), or at least one agent configured to inhibit scarring or fibrosis on or around at least a portion of the tube.

16. The apparatus of claim 1, wherein the tube is configured to protect the second set of stimulation elements from fibrosis tissue formed after the implantation procedure and to be removed from the stimulation assembly to remove the fibrosis tissue during the subsequent procedure after the implantation procedure.

17. The apparatus of claim 16, wherein the stimulation assembly is configured to be inserted into the cochlea to a first angular insertion depth during the implantation procedure and to be further inserted into the cochlea to a second angular insertion depth during the subsequent procedure, the second angular insertion depth greater than the first angular insertion depth.

18. The apparatus of claim 16, wherein the inner layer portion and the outer layer portion are configured to remain on the stimulation assembly after the implantation procedure and to be unwrapped from the stimulation assembly during the subsequent procedure.

19. The apparatus of claim 16, wherein the inner layer portion and the outer layer portion are configured to remain intact after the implantation procedure and to be unwrapped from the stimulation assembly during the subsequent procedure.

20. A method comprising:
providing an elongate stimulation assembly comprising:
a plurality of stimulation elements configured to stimulate spiral ganglion cells of a cochlea of a recipient; and
a tube covering some of the stimulation elements but fewer than all of the stimulation elements;
implanting the stimulation assembly within the cochlea of a recipient such that the tube is positioned externally to the cochlea and the stimulation assembly is positioned within the cochlea so as to allow residual hearing in a first frequency range using the cochlea while the stimulation assembly is configured to assist hearing in a second frequency range using the cochlea, the second frequency range higher than the first frequency range; and
removing the tube from the stimulation assembly after the stimulation assembly allows the residual hearing in the first frequency range using the cochlea and assists the hearing using the cochlea in the second frequency range.

21. The method of claim 20, further comprising:
moving the stimulation assembly further into the cochlea such that the stimulation assembly is configured to assist hearing using the cochlea in the first frequency range and the second frequency range.

22. The method of claim 21, wherein implanting the stimulation assembly comprises, during a first surgical procedure, inserting the stimulation assembly through an opening in the cochlea and forming a seal between the tube and the cochlea, the seal configured to prevent bacteria from entering the cochlea through the opening.

23. The method of claim 22, wherein removing the tube from the stimulation assembly and moving the stimulation assembly further into the cochlea are performed during a second surgical procedure, the second surgical procedure less invasive than the first surgical procedure.

24. The method of claim 20, wherein the plurality of stimulation elements comprising a first set of stimulation elements not covered by the tube and a second set of stimulation elements covered by the tube.

25. The method of claim 24, further comprising moving the stimulation assembly further into the cochlea such that both the first set of stimulation elements and the second set of stimulation elements are positioned within the cochlea.

26. The method of claim 25, wherein removing the tube comprises peeling, tearing, ripping, or unwrapping the tube from the stimulation assembly.

27. The method of claim 20, wherein the tube comprises at least one antimicrobial agent and the method further comprises releasing the at least one antimicrobial agent from the tube.

28. The method of claim 20, wherein implanting the stimulation assembly comprises inserting the stimulation assembly through an opening in the cochlea and positioning the stimulation assembly such that a first end of the tube is proximal to the opening.

29. The method of claim 28, wherein implanting the stimulation assembly further comprises forming a seal between the tube and the cochlea, the seal configured to prevent bacteria from entering the cochlea through the opening.

30. The method of claim 28, wherein the opening comprises a cochleostomy or a round window of the cochlea.

31. The method of claim 20, wherein said removing the tube comprises removing biological matter from the stimulation assembly.

* * * * *